US010463266B2

(12) United States Patent
Wilson

(10) Patent No.: US 10,463,266 B2
(45) Date of Patent: Nov. 5, 2019

(54) NEURAL MONITORING METHODS AND SYSTEMS FOR TREATING PHARYNGEAL DISORDERS

(71) Applicant: MED-EL Elektromedizinische Geraete GmbH, Innsbruck (AT)

(72) Inventor: Willard Wilson, Eden Prairie, MN (US)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 15/623,712

(22) Filed: Jun. 15, 2017

(65) Prior Publication Data

US 2017/0347904 A1 Dec. 7, 2017

Related U.S. Application Data

(62) Division of application No. 13/752,273, filed on Jan. 28, 2013, now Pat. No. 9,706,934.
(Continued)

(51) Int. Cl.
*A61B 5/04* (2006.01)
*A61B 7/00* (2006.01)
(Continued)

(52) U.S. Cl.
CPC ........ *A61B 5/04001* (2013.01); *A61B 5/0826* (2013.01); *A61B 5/7278* (2013.01);
(Continued)

(58) Field of Classification Search
CPC .................. A61B 5/00; A61B 5/04001; A61B 5/04012–04018; A61B 5/0488; A61B 5/04886; G06F 19/30
(Continued)

(56) References Cited

U.S. PATENT DOCUMENTS 4,289,142 A 9/1981 Kearns
4,702,254 A 10/1987 Zabara
(Continued)

FOREIGN PATENT DOCUMENTS

CN 1638836 A 7/2005
CN 1819855 A 8/2006
(Continued)

OTHER PUBLICATIONS

Dozier et al., "Coordination of swallowing and respiration in normal sequential cup swallows," Laryngoscope, vol. 116, pp. 1489-1493, 2006.
(Continued)

*Primary Examiner* — Carl H Layno
*Assistant Examiner* — Dacheng Xie
(74) *Attorney, Agent, or Firm* — Sunstein Kann Murphy & Timbers LLP

(57) ABSTRACT

Methods and systems for monitoring, preventing and/or treating upper airway disorders such as apnea, dysphagia, reflux and/or snoring are described. The methods and systems monitor the upper airway disorders by processing one or more neural signals obtained from one or more upper airway afferents. Upper airway disorders are prevented and/or treated by delivering one or more stimulations to one or more reflex-related afferents, efferents, muscles, and sensory receptors to manipulate the threshold and/or trigger an upper airway reflex including, but not limited to a swallow reflex and/or a negative-pressure reflex.

19 Claims, 13 Drawing Sheets

Related U.S. Application Data

(60) Provisional application No. 61/591,078, filed on Jan. 26, 2012.

(51) Int. Cl.

| | | |
|---|---|---|
| *A61B 5/00* | (2006.01) | |
| *A61B 5/08* | (2006.01) | |
| *A61H 31/00* | (2006.01) | |
| *A61N 1/36* | (2006.01) | |
| *A61B 5/085* | (2006.01) | |
| *A61B 5/0205* | (2006.01) | |

(52) U.S. Cl.
CPC .............. *A61B 7/003* (2013.01); *A61B 7/008* (2013.01); *A61H 31/00* (2013.01); *A61N 1/3601* (2013.01); *A61N 1/36007* (2013.01); *A61B 5/0205* (2013.01); *A61B 5/085* (2013.01); *A61B 5/0816* (2013.01); *A61B 5/0823* (2013.01); *A61B 5/4205* (2013.01); *A61B 5/4211* (2013.01); *A61B 5/4818* (2013.01); *A61B 5/4836* (2013.01); *A61B 5/7282* (2013.01); *A61N 1/36053* (2013.01); *A61N 1/36057* (2013.01)

(58) Field of Classification Search
USPC ......................................................... 600/300
See application file for complete search history.

(56) References Cited

U.S. PATENT DOCUMENTS

| | | | |
|---|---|---|---|
| 4,830,008 | A | 5/1989 | Meer |
| 5,146,918 | A | 9/1992 | Kallok et al. |
| 5,485,851 | A | 1/1996 | Erickson |
| 5,824,027 | A | 10/1998 | Hoffer et al. |
| 5,913,831 | A | 6/1999 | Breneman |
| 6,587,725 | B1 | 7/2003 | Durand et al. |
| 6,758,216 | B1 | 7/2004 | Berthon-Jones et al. |
| 7,117,032 | B2 | 10/2006 | Childre et al. |
| 7,282,980 | B2 | 10/2007 | Baru |
| 7,340,302 | B1 | 3/2008 | Falkenberg et al. |
| 7,359,837 | B2 | 4/2008 | Drew |
| 7,371,220 | B1 | 5/2008 | Koh et al. |
| 7,672,728 | B2 | 3/2010 | Libbus et al. |
| 9,706,934 | B2 | 7/2017 | Wilson |
| 2005/0085866 | A1* | 4/2005 | Tehrani ................ A61N 1/3601 607/42 |
| 2005/0113703 | A1 | 5/2005 | Farringdon et al. |
| 2005/0131288 | A1 | 6/2005 | Turner et al. |
| 2005/0222522 | A1 | 10/2005 | Heruth et al. |
| 2006/0094970 | A1 | 5/2006 | Drew |
| 2006/0189881 | A1 | 8/2006 | Fassio |
| 2006/0195144 | A1 | 8/2006 | Giftakis et al. |
| 2006/0224211 | A1 | 10/2006 | Durand et al. |
| 2007/0150006 | A1 | 6/2007 | Libbus et al. |
| 2007/0156179 | A1 | 7/2007 | S.E. |
| 2007/0255330 | A1 | 11/2007 | Lee et al. |
| 2008/0033490 | A1 | 2/2008 | Giftakis et al. |
| 2008/0058892 | A1 | 3/2008 | Haefner et al. |
| 2008/0065184 | A1 | 3/2008 | Hoffer et al. |
| 2008/0110461 | A1 | 5/2008 | Mulqueeny et al. |
| 2008/0167539 | A1 | 7/2008 | Teller et al. |
| 2008/0195179 | A1 | 8/2008 | Quick |
| 2008/0200959 | A1 | 8/2008 | Libbus et al. |
| 2008/0269625 | A1 | 10/2008 | Halperin et al. |
| 2009/0036777 | A1 | 2/2009 | Zhang et al. |
| 2009/0050155 | A1 | 2/2009 | Alder et al. |
| 2009/0187124 | A1 | 7/2009 | Ludlow et al. |
| 2010/0016908 | A1 | 1/2010 | Martin et al. |
| 2010/0125310 | A1* | 5/2010 | Wilson ................ A61N 1/0556 607/42 |
| 2010/0242967 | A1 | 9/2010 | Burbank et al. |
| 2010/0312302 | A1 | 12/2010 | Zealear |
| 2011/0190642 | A1 | 8/2011 | Alt et al. |

FOREIGN PATENT DOCUMENTS

| | | |
|---|---|---|
| CN | 101569527 A | 11/2009 |
| CN | 101716394 A | 6/2010 |
| CN | 101743036 A | 6/2010 |
| WO | 02066111 A1 | 8/2002 |
| WO | 2008005903 A2 | 1/2008 |
| WO | 2008025155 A1 | 3/2008 |
| WO | 2008046190 A1 | 4/2008 |
| WO | 2010057286 A1 | 5/2010 |
| WO | 2011016864 A1 | 2/2011 |
| WO | 2013113023 A1 | 8/2013 |

OTHER PUBLICATIONS

Dua et al., "Safety and feasibility of evaluating airway-protective reflexes during sleep: new technique and preliminary results," Gastrointestinal Endoscopy., vol. 65, No. 3, pp. 483-486, 2007.

Gheshmy et al., "Chronic hypercapnia modulates respiratory-related central pH/CO2 chemoreception in an amphibian, *Bufo marinus*," Journal of Experimental Biology, vol. 209, pp. 1135-1146, 2006.

Jobin et al., "Swallowing function and upper airway sensation in obstructive sleep apnea," Journal of Applied Physiology, vol. 102, pp. 1587-1594, 2007.

Page et al., "Airway Protection in Sleeping Infants in Response to Pharyngeal Fluid Stimulation in the Supine Position," Pediatric Research, vol. 44, No. 5, pp. 691-698, 1998.

Purves et al., "Pain," Neuroscience, 3rd Edition, Sinauer, Sunderland, Mass., Ch. 9, pp. 209-212, 2004.

Saito et al., "Swallowing-related activities of respiratory and non-respiratory neurons in the nucleus of solitary tract in the rat," Journal of Physiology, vol. 540, pp. 1047-1060, 2002.

Teramoto et al., "Impaired swallowing reflex in patients with obstructive sleep apnea syndrome," Chest, vol. 116, pp. 17-21, 1999.

Weaver et al., "Adherence to continuous positive airway pressure therapy: the challenge to effective treatment," Proceedings of the American Thoracic Society, vol. 5, pp. 173-178, 2008.

International Search Report regarding PCT/CA2007/001784, 4 pages, dated Jan. 28, 2008.

International Search Report regarding PCT/CA2008/002036, 3 pages, dated Jul. 28, 2009.

Supplemental European Search Report regarding EP07855411.0, 10 pages, dated Jul. 11, 2011.

International Search Report regarding PCT/US2011/36653, 17 pages, dated Aug. 26, 2011.

International Search Report and Written Opinion regarding PCT/US13/23488, 18 pages, dated Jun. 14, 2013.

Supplementary Partial European Search Report, Application No. EP 13740943, 7 pages, dated Aug. 20, 2015.

Supplementary Partial European Search Report, Application No. EP 13740943, 13 pages, dated Dec. 1, 2015.

Bugaev et al., "Prothrombotic Markers in Patients with Arterial Hypertension and Obstructive Sleep Apnea Syndrome," Journal of Sleep & Medicine Disorders 2(4): 1029, pp. 1-4, 2015.

\* cited by examiner

NEURAL MONITORING METHODS AND SYSTEMS FOR TREATING PHARYNGEAL DISORDERS

CROSS REFERENCE TO RELATED APPLICATIONS

This application is a divisional of U.S. application Ser. No. 13/752,273 filed Jan. 28, 2013, issued on Jul. 18, 2017 as U.S. Pat. No. 9,706,934, which claims benefit of U.S. Provisional Patent Application No. 61/591,078 filed Jan. 26, 2012 and entitled "Neural Monitoring Methods and Systems for Treating Pharyngeal Disorders," the disclosures of which are hereby incorporated herein by reference in their entirety.

FIELD OF THE INVENTION

The invention generally relates to neural monitoring methods and systems for detecting, identifying and treating upper airway disorders such as sleep apnea/hypopnea, dysphagia, reflux, and/or snoring.

BACKGROUND OF THE INVENTION

The pharynx serves multiple and diverse roles—mastication, breathing, swallowing, speaking, taste and smell, heat, humidify and filter air, protect airway. This single structure serves diverse and highly complex functions, many of which may not be carried out simultaneously. For example, the pharynx is a structure shared by both the respiratory and digestive pathways and acts as a mechanical "switch" to direct incoming air and solids to the appropriate anatomical systems during breathing and swallowing.

During normal respiration, structures of the pharynx assume positions that maximize the patency of the airway. As air is inhaled, tonic activation actively maintains pharyngeal position and phasic activation via the negative pressure reflex resists vacuum-induced changes in pharyngeal position. During normal swallowing, the pharynx propels food and fluid caudally while simultaneously positioning the airway to prevent aspiration of the food and fluid materials into the lungs. Indeed, swallowing is a coordinated pattern of activity involving more than 50 muscles throughout the upper airway and is generally divided into oral, pharyngeal, and esophageal phases.

Because the pharynx is situated at the literal crossroad of the respiratory and gastrointestinal intakes, pharyngeal structural and/or postural dysfunction may result in a variety of disorders including obstructive sleep apnea, dysphagia, snoring, and acid reflux/GERD. In addition to the immediate health concerns introduced by this assemblage of disorders, many of these disorders are associated with an increased risk of additional comorbidities such as heart attack, stroke, hypertension, diabetes, development of carotid artery atherosclerosis, pulmonary aspiration and aspiration pneumonia, among others.

Existing treatments for pharyngeal disorders such as apnea include continuous positive air pressure (CPAP) devices, surgical interventions, weight loss, medication, changes in sleeping position and/or dental appliances; many of these treatments suffer from limited effectiveness or compliance. Implantable monitor devices are under development that monitor thoracic pressure, blood oxygenation, or the bioelectric activity of the diaphragm, intercostal muscles, upper airway muscles, or the efferent nerves associated with these muscles. Other implantable devices have been described that terminate apnea using drug delivery, atrial overdrive pacing or electrical stimulation of the nerves or muscles that control respiratory activities. To date, the potential for the development of effective methods of preventing and/or treating disorders associated with pharyngeal dysfunction remains unfulfilled.

A need in the art exists for additional methods of detecting, preventing, and/or treating adverse pharyngeal conditions and/or treating pharyngeal disorders such as sleep apnea, snoring, dysphagia and/or GERD.

SUMMARY OF THE INVENTION

According to the invention, a method for monitoring a condition in a subject is provided. The method comprises obtaining one or more neural signals from one or more upper airway afferents of the subject; processing each of the one or more neural signals to obtain at least one neural activity profile; comparing each of the at least one neural activity profiles to one or more activity criteria to associate each neural activity profile with an associated activity type; and processing each of the at least one neural activity profiles to determine an activity state characterizing the associated activity type.

Each neural activity profile may be characterized by at least one of: a neural signal timing, a neural signal amplitude, a neural signal phase, a neural signal position, a neural signal conduction velocity, and any combination thereof.

An associated activity type may be chosen from a respiratory activity type, a deglutition activity type, a vibration activity type, a reflux activity type, and any combination thereof.

The activity state may comprise: a respiratory state comprising respiratory timing, respiratory amplitude, respiratory phase, respiratory location, and any combination thereof; a deglutition state comprising solid contact, fluid contact, contact velocity, contact timing, contact amplitude, contact pressure, contact texture, contact temperature, a presence of a unswallowed bolus, and any combination thereof; a vibration state comprising vibration timing, vibration amplitude, vibration phase, vibration location, vibration pattern, and any combination thereof; and a reflux state comprising reflux timing, reflux pH, reflux location, and any combination thereof.

The one or more upper airway afferents may be chosen from pharyngeal afferents, laryngeal afferents, oral cavity afferents and nasal cavity afferents.

The one or more activity criteria may comprise: a respiratory criterion indicating a respiratory activity, a deglutition criterion indicating a deglutition activity, a vibration criterion indicating a vibration activity, and a reflux criterion. The respiratory criterion may comprise a time separation between peak neural signal amplitudes ranging from about 1 seconds to about 5 seconds, a periodically repeating pattern of neural signals with a period ranging from about 12 patterns per minute to about 60 patterns per minute, and any combination thereof. The deglutition criterion may comprise an anterior to posterior neural activation pattern, a stereotyped neural activation pattern with a duration of less than about 1 second, and any combination thereof. The vibration criterion may comprise a neural signal frequency ranging from about 10 Hz to about 400 Hz, a time separation between peak neural signal amplitudes ranging from about 1 second to about 5 seconds, and any combination thereof. The reflux criterion may comprise a signal conduction velocity of less than about 2 m/s.

Processing the one or more neural signals may further comprise analyzing a timing sequence of two or more activity patterns, wherein each of the two or more activity patterns is obtained from different upper airway afferents.

The method for monitoring a condition in a subject may further comprise processing the at least one activity state to obtain at least one condition of the subject. The at least one condition of the subject may be chosen from a respiratory condition, a deglutition condition, a vibration condition, a reflux condition, and any combination thereof. The respiratory condition may comprise apnea, tachypnea, hyperpnea, hypopnea, polypnea, dyspnea, bradypnea, cough, Cheyne-Stokes respiration, Biot's respiration, ataxic respiration, Kussmaul respiration, wheezing, irregular respiration, respiratory arrest, restrictive respiration, shallow breathing, hypoventilation and any combination thereof. The deglutition condition may comprise presence of unswallowed bolus, occurrence of swallow, occurrence of dysphagic swallow, presence of acid reflux, and any combination thereof. The vibration condition may comprise snoring, stridor, wheezing vocalization, and any combination thereof. The reflux condition may comprise esophageal reflux, pharyngeal reflux, laryngeal reflux and any combination thereof.

Alternatively, or in combination with the above, the method may further comprise assessing the at least one condition to predict a disorder. The disorder may be chosen from obstructive apnea, central apnea, mixed apnea, snoring, flow limitation, dysphagia, heart failure, uremia, asthma, cardiac arrest, organ failure, metabolic acidosis, COPD, pulmonary embolism, Ondine's curse, obesity hypoventilation syndrome, laryngeal penetration, aspiration, esophageal reflux, laryngeal reflux, presence of unswallowed bolus, acid reflux, GERD, laryngeal penetration, aspiration, and any combination thereof.

Any one or more of the at least one states, the at least one conditions, the at least one disorders, and any combination thereof may be displayed on a patient monitor device.

Any one or more of the at least one states, the at least one conditions, the at least one disorders, and any combination thereof may be communicated to a treatment system.

The invention also provides a system for monitoring a condition in a subject. The system may comprise at least one processor; a Cardio Respiratory Monitoring (CRM) containing a subject monitor application comprising a plurality of modules executable on the at least one processor; and a GUI module for generating one or more forms used to receive inputs to the system and to deliver output from the system. The plurality of modules may comprise: a neural signal acquisition module for obtaining one or more neural signals in one or more upper airway afiferents of the subject; a neural activity profile module for processing each of the one or more neural signals to obtain at least one neural activity profile; an activity type module for comparing each of the at least one neural activity profiles to one or more activity criteria to associate each neural activity profile with an associated activity type; and an activity state module for processing each of the at least one neural activity profiles to determine an activity state characterizing the associated activity type. Each neural activity profile, activity type, and activity state may be characterized as described above. Suitable activity criteria are also described above.

The neural activity profile module may further analyze a timing sequence of two or more activity patterns, wherein each of the two or more activity patterns is obtained from different upper airway afferents.

The plurality of modules may further comprise a condition module for processing the at least one activity state to obtain at least one condition of the subject. The at least one condition of the subject may be chosen from a respiratory condition, a deglutition condition, a vibration condition, a reflux condition, and any combination thereof. Suitable respiratory, deglutition, vibration, and reflux conditions are described above.

Alternatively, or in combination with the above, the system may further comprise a disorder prediction module for assessing the at least one condition to predict a disorder. The disorder may be chosen from obstructive apnea, central apnea, mixed apnea, snoring, flow limitation, dysphagia, heart failure, uremia, asthma, cardiac arrest, organ failure, metabolic acidosis, COPD, pulmonary embolism, Ondine's curse, obesity hypoventilation syndrome, laryngeal penetration, aspiration, esophageal reflux, laryngeal reflux, pharyngeal reflux, presence of unswallowed bolus, acid reflux, GERD and any combination thereof.

The invention also provides a first method for treating and/or preventing a disorder in a subject in need thereof. The method comprises delivering at least one stimulation to modulate at least one reflex chosen from a swallowing reflex, a negative-pressure reflex, and any combination thereof. The disorder comprises at least one of: obstructive apnea, central apnea, obesity hypoventilation syndrome, dysphagia, esophageal reflux, presence of unswallowed bolus, acid reflux, GERD, and any combination thereof. Each of the at least one stimulations is delivered with subthreshold parameters insufficient to independently elicit the reflex or with suprathreshold parameters sufficient to independently elicit the reflex. The at least one stimulation is delivered according to a delivery schedule chosen from periodic, random, and continuous.

Each of the at least one stimulations may comprise an electrical stimulation or a mechanical stimulation.

Each electrical stimulation may be delivered to a reflex-related nerve, a reflex-related muscle, a reflex-related sensory receptor, and any combination thereof. Each mechanical stimulation may be delivered to a reflex-related sensory receptor.

The reflex-related nerve may comprise an afferent or an efferent. An afferent may be chosen from: superior laryngeal nerve, internal branch of the superior laryngeal nerve, recurrent laryngeal nerve, pharyngeal branch of vagus nerve, pharyngeal branch of glossopharyngeal nerve, tonsilar branch of glossopharyngeal nerve, lingual branch of glossopharyngeal nerve, pharyngeal plexus, intermediate nerve, palatine nerve, greater petrosal nervepterygopalatine nerve, pterygopalatine ganglion, pharyngeal branch of the pterygopalatine ganglion, superior alveolar nerve, buccal nerve, greater petrosal nerve, maxillary branch of the trigeminal nerve, posterior nasal branch of the maxillary nerve, nasociliary nerve, posterior ethmoidal nerve, infratrochlear nerve, anterior ethmoidal nerve, nasopalatine nerve, greater palatine nerve, lesser palatine nerve, or infraorbital nerve. An efferent may be chosen from: recurrent laryngeal nerve, external branch of superior laryngeal nerve, brancial motor branch of glossopharyngeal nerve and proximal fibers, mandibular nerve, medial pterygoid nerve, pharyngeal branch of vagus nerve and proximal fibers; branch of facial nerve and proximal fibers, and branch of hypoglossal nerve and proximal fibers.

The reflex-related sensory receptor may be situated in skin or mucosa of the subject, and may be chosen from: a mechanoreceptor sensitive to negative airway pressure, positive airway pressure, stretch, position, shear, slip, vibration, texture, touch, mechanical compression, muscle stretch, muscle drive, air flow, blood pressure or blood osmolarity; a chemoreceptor sensitive to $CO_2$, $O_2$, or pH; a thermoreceptor sensitive to temperature or airflow; and a nociceptor sensitive to polymodal pain.

Each of the at least one stimulations may be chosen from: a subthreshold electrical stimulation delivered to the reflex-related nerve or to the reflex-related sensory receptor to reduce the threshold of the reflex, to maintain muscle tone, and any combination thereof; a subthreshold electrical stimulation delivered to the reflex-related muscle to maintain muscle tone; a subthreshold mechanical stimulation delivered to the reflex-related sensory receptor to reduce the threshold of the at least one reflex; a suprathreshold electrical stimulation delivered to the reflex-related nerve, the reflex-related sensory receptor, the reflex-related muscle, or any combination thereof to maintain muscle tone, position and/or posture of one or more respiratory and/or deglutition structures of the subject; a suprathreshold mechanical stimulation delivered to the reflex-related sensory receptor to maintain muscle tone, position and/or posture of one or more respiratory and/or deglutition structures of the subject; a suprathreshold electrical stimulation delivered to the reflex-related nerve, the reflex-related sensory receptor, the reflex-related muscle, or any combination thereof to treat the disorder; and a suprathreshold mechanical stimulation delivered to the reflex-related sensory receptor to treat the disorder.

Each of the at least one stimulations is delivered either according to a predetermined schedule, in response to at least one stimulation signal, and any combination thereof.

The at least one stimulation signal may be received from a patient monitor device.

The first method for treating and/or preventing a disorder in a subject in need thereof may further comprise assessing at least one condition of the subject chosen from a respiratory condition, a deglutition condition, a vibration condition, a reflux condition, and any combination thereof to predict the occurrence of the disorder in the subject. Suitable respiratory, deglutition, vibration, and reflux conditions are described above.

The first method for treating and/or preventing a disorder in a subject in need thereof may further comprise obtaining one or more neural signals from one or more upper airway afferents of the subject; processing each of the one or more neural signals to obtain at least one neural activity profile; comparing each of the at least one neural activity profiles to one or more activity criteria to associate each neural activity profile with an associated activity type; processing each of the at least one neural activity profiles to determine an activity state characterizing the associated activity type; and processing the activity state of the subject to obtain the at least one condition of the subject. Each neural activity profile, activity type, and activity state may be characterized as described above.

The first method for treating and/or preventing a disorder in a subject in need thereof may further comprise generating the at least one stimulation signal when: the disorder is predicted to time the delivery of the at least one stimulation to coincide with an occurrence of the disorder; the respiratory phase is an exhalation phase to time the delivery of the at least one stimulation to coincide with an exhalation of the subject; and any combination thereof.

The invention also provides a first system for treating and/or preventing a disorder in a subject. The system may comprise at least one processor and a Cardio Respiratory Monitoring (CRM) containing a disorder treatment application comprising a plurality of modules executable on the at least one processor. The plurality of modules may comprise: a reflex stimulation module for delivering at least one stimulation to modulate at least one reflex chosen from a swallowing reflex, a negative pressure reflex, and any combination thereof and a GUI module for generating one or more forms used to receive inputs to the system and to deliver output from the system. The disorder may be chosen from obstructive apnea, central apnea, snoring, mixed apnea, flow limitation, obesity hypoventilation syndrome, dysphagia, esophageal reflux, presence of unswallowed bolus, acid reflux, GERD, and any combination thereof. Each of the at least one stimulations is delivered at an intensity chosen from subthreshold stimulus parameters intensity insufficient to independently elicit the reflex and suprathreshold stimulus parameters sufficient to independently elicit the reflex. The at least one stimulation is delivered according to a delivery schedule chosen from periodic, random, and continuous.

Each of the one stimulations may comprise an electrical stimulation or a mechanical stimulation, as described above.

The plurality of modules may further comprise a stimulation timing module for timing the delivery of each of the at least one stimulations according to a predetermined schedule, in response to at least one stimulation signal, and any combination thereof.

The at least one stimulation signal may be received from a patient monitor system.

The plurality of modules may further comprise a disorder prediction module for assessing at least one condition of the subject chosen from a respiratory condition, a deglutition condition, a vibration condition, a reflux condition, and any combination thereof to predict the occurrence of the disorder in the subject. Suitable respiratory, deglutition, vibration, and reflux conditions are described above.

The plurality of modules may further comprise a neural signal acquisition module for obtaining one or more neural signals from one or more upper airway afferents of the subject; a neural activity profile module for processing each of the one or more neural signals to obtain at least one neural activity profile; and an activity type module for comparing each of the at least one neural activity profiles to one or more activity criteria to associate each neural activity profile with an associated activity type. Each neural activity profile and activity type may be characterized as described above.

The stimulation timing module may generate the at least one stimulation signal when: the disorder prediction module predicts the disorder in order to time the delivery of the at least one stimulation to coincide with an occurrence of the disorder; the activity state module determines that the respiratory phase is an exhalation phase, to time the delivery of the at least one stimulation to coincide with an exhalation of the subject; and any combination thereof.

The invention also provides a second method for treating and/or preventing a disorder in a subject in need thereof. The method may comprise obtaining one or more neural signals from one or more upper airway afferents of the subject; processing each of the one or more neural signals to obtain at least one neural activity profile; comparing each of the at least one neural activity profiles to one or more activity criteria to associate each neural activity profile with an associated activity type; processing each of the at least one neural activity profiles to determine an activity state characterizing the associated activity type; processing the activity state of the subject to obtain the at least one condition of the subject; assessing the at least one condition to predict a disorder chosen from obstructive apnea, central apnea, obesity hypoventilation syndrome, dysphagia, esophageal reflux, presence of unswallowed bolus, acid reflux, GERD, and any combination thereof and delivering at least one stimulation to modulate at least one reflex chosen from a swallowing reflex, a negative-pressure reflex, and any combination thereof.

Each of the one stimulations may comprise an electrical stimulation or a mechanical stimulation, as described above.

Each neural activity profile, activity type, and activity state may be characterized as described above.

The at least one condition of the subject may be chosen from a respiratory condition, a deglutition condition, a vibration condition, a reflux condition, and any combination thereof. Suitable respiratory, deglutition, vibration, and reflux conditions are described above, as are suitable activity criteria.

Processing the one or more neural signals further comprises analyzing a timing sequence of two or more activity patterns, wherein each of the two or more activity patterns is obtained from different upper airway afferents.

Each of the at least one stimulations is delivered either according to a predetermined schedule, in response to at least one stimulation signal, and any combination thereof.

The second method for treating and/or preventing a disorder in a subject in need thereof may further comprise displaying any one or more of the at least one states, the at least one conditions, the at least one disorders, and any combination thereof on a patient monitor device.

The second method for treating and/or preventing a disorder in a subject in need thereof may further comprise generating the at least one stimulation signal when: the disorder is predicted, to time the delivery of the at least one stimulation to coincide with an occurrence of the disorder; the respiratory phase is an exhalation phase, to time the delivery of the at least one stimulation to coincide with an exhalation of the subject; and any combination thereof.

The invention also provides a second system for treating and/or preventing a disorder in a subject The system may comprise at least one processor; a Cardio Respiratory Monitoring (CRM) containing a disorder treatment application comprising a plurality of modules executable on the at least one processor; and a GUI module for generating one or more forms used to receive inputs to the system and to deliver output from the system. The plurality of modules may comprise: (i) a neural signal acquisition module for obtaining one or more neural signals in one or more upper airway afferents of the subject; (ii) a neural activity profile module for processing each of the one or more neural signals to obtain at least one neural activity profile; (iii) an activity type module for comparing each of the at least one neural activity profiles to one or more activity criteria to associate each neural activity profile with an associated activity type; (iv) an activity state module for processing each of the at least one neural activity profiles to determine an activity state characterizing the associated type; (v) a condition module for processing the at least one activity states to obtain at least one condition of the subject chosen from a respiratory condition, a deglutition condition, a condition, a reflux condition, and any thereof; (vi) a disorder prediction module for assessing the at least one condition to predict a disorder chosen from: from obstructive apnea, central apnea, obesity hypoventilation syndrome, dysphagia, esophageal reflux, presence of unswallowed bolus, acid reflux, GERD, and any combination thereof; (vii) a reflex stimulation module for delivering at least one stimulation to modulate at least one reflex chosen from a swallowing reflex, a negative-pressure reflex, and any combination thereof, wherein: each of the at least one stimulations is delivered at parameters chosen from subthreshold parameters insufficient to independently elicit the reflex and suprathreshold parameters sufficient to independently elicit the reflex; and the at least one stimulation is delivered according to a delivery schedule chosen from periodic, random, and continuous; and (viii) a stimulation timing module for timing the delivery of each of the at least one stimulations according to a predetermined schedule, in response to at least one stimulation signal, and any combination thereof. Each neural activity profile, activity type, and activity state may be characterized as described above. Suitable respiratory, deglutition, vibration, and reflux conditions are also described above, as are suitable activity criteria.

The neural activity profile module may further analyze a timing sequence of two or more activity patterns, wherein each of the two or more activity patterns is obtained from different upper airway afferents.

Each of the one stimulations may comprise an electrical stimulation or a mechanical stimulation, as described above.

The at least one stimulation signal may be received from a monitor system.

The stimulation timing module may generate the at least one stimulation signal when: the disorder prediction module predicts the disorder in order to time the delivery of the at least one stimulation to coincide with an occurrence of the disorder; the activity state module determines that the respiratory phase is an exhalation phase, to time the delivery of the at least one stimulation to coincide with an exhalation of the subject; and any combination thereof.

Other aspects and features of the disclosure are described more thoroughly below.

Other aspects and features of the disclosure are described more thoroughly below.

BRIEF DESCRIPTION OF THE DRAWINGS

Exemplary embodiments are illustrated in referenced figures of the drawings. It is intended that the embodiments and figures disclosed herein are to be considered illustrative rather than limiting.

Corresponding reference characters and labels indicate corresponding elements among the view of the drawings. The headings used in the figures should not be interpreted to limit the scope of the claims.

DETAILED DESCRIPTION OF THE INVENTION

Figure 1:
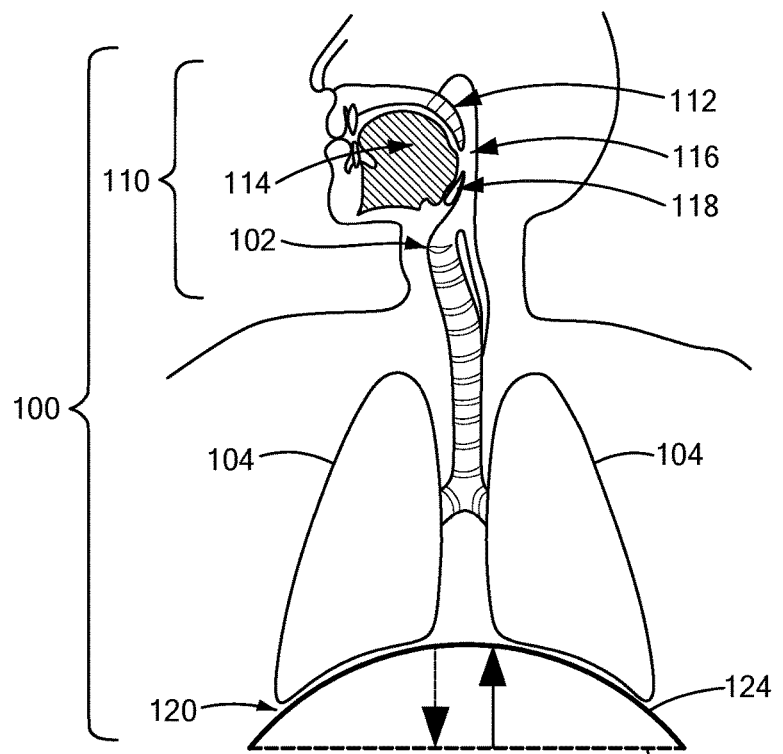
FIG. 1 is a schematic representation of the human airway relevant to upper airway pressure as measured at the larynx during normal respiration.

A novel method of monitoring an upper airway condition in a patient including, but not limited to a respiratory condition such as apnea, a deglutition (swallowing) condition such as dysphagia, a vibration condition such as snoring, and/or a reflux condition such as GERD is provided that includes processing one or more neural signals obtained from one or more upper airway afferents. It has been discovered that neural signals carried by upper airway afferent nerves including, but not limited to, the internal branch of the superior laryngeal nerve (iSLN) may be processed to extract information that may be used to monitor the respiratory, deglutition, vibratory, and/or reflux status of the pharynx and to detect and characterize adverse conditions. Upper airway afferent neural signals may be obtained and processed using aspects of the method described herein below to detect and characterize such diverse conditions as sleep apnea, heart failure, hypoventilation syndrome, dysphagia, acid reflux, and snoring.

Embodiments of the method exploit the normal function and organization of the peripheral nervous system by monitoring the activity of sensory nerve fibers. By tapping into the neural communication between the body's own biological sensors and central nervous system, the method can directly monitor the intrinsic sensor set of the subject that gives rise to the sensory percepts and the physiological responses to stimulation of the innervated area.

In addition to the iSLN, other upper airway afferents including, but not limited to glossopharyngeal afferents (pharyngeal, tonsilar and lingual branches of glossopharyngeal nerve), and other vagus afferents (pharyngeal branch of vagus nerve) may be used to monitor could be used to monitor upper airway conditions. In various other embodiments, two or more upper airway afferents may be monitored simultaneously. In these other methods, the processing of neural signals from multiple upper airway afferents increases the surface area of pharyngeal mucosa monitored, potentially resulting in more sensitive detection and localization of any obstructions or other anomalies. In addition, the simultaneous monitoring of multiple afferents may allow for spatial and/or temporal patterns of activity associated with upper airway conditions such as apnea and/or dysphagia/swallowing to be characterized and to further allow for the development of a tailored therapy based on the measured spatial/temporal pattern. Further, the expanded selection of upper airway afferents available for use in various aspects of the method may result in enhanced surgical access for placement of neural activity measurement devices including, but not limited to nerve cuffs.

Section headings as used herein are not intended to be limiting in scope.

I. Definitions

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

The use of "or" means "and/or" unless stated otherwise. Furthermore, the use of the term "including", as well as other forms, such as "includes" and "included", is not limiting.

As used herein, unless specified otherwise, the term "apnea" encompasses any form of involuntary apnea, bradypnea or hypopnea of obstructive, central or mixed origin, including sleep apnea and sleep hypopnea, and also includes any complex episode of apnea or hypopnea occurring during sleep or wakefulness, as in Cheyne-Stokes respiration.

As used herein to describe a nerve or muscle, the term "swallow-related" refers to the nerve or a muscle as one for which normal function includes activity that effects, or contributes to effecting, all or any part of a normal oropharyngeal swallow sequence, wherein a swallow sequence refers to that reflexive and centrally programmed series of muscle movements beginning with muscle movements in an oral phase under voluntary muscular control and proceeding with pharyngeal and esophageal phases under involuntary neuromuscular control.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamster, guinea pig, cat, dog, rat, mouse, non-human primate (including but not limited to a monkey, such as a cynomolgous monkey, rhesus monkey, and chimpanzee), and a human). Preferably, the subject is a human.

As used herein, the term "apnea"," is defined to mean either an obstructive, central, mixed, or complex episode of apnea or hypopnea, occurring during sleep or when awake as in Cheyne-Stokes respiration.

As used herein, the term "snoring" refers to a pharyngeal vibratory state. As used herein, the term "nerve" refers to the nerve fibers contained therein including those fibers in the trunk proximal to that nerve and those nerve fibers in the branches distal to that nerve.

Unless otherwise defined herein, scientific and technical terms used in connection with the present disclosure shall have the meanings that are commonly understood by those of ordinary skill in the art. For example, any nomenclatures used in connection with, and techniques of, neural science, electrophysiology, animal and cellular anatomy, cell and tissue culture, molecular biology, immunology, and microbiology described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

II. Methods of Monitoring, Preventing, and/or Treating an Upper Airway Condition/Disorder

1. Overview

In various aspects, a system and method of monitoring an upper airway condition or disorder processes at least one neural signal obtained from an upper airway afferent of the subject and extracts information characterizing an upper airway condition. In other aspects, this information may be further analyzed to predict an upper airway disorder. The parameters resulting from the implementation of this system and method in various aspects may be communicated to a display, and/or these parameters may be transferred to a display device, a patient monitor, and/or a treatment device. In yet other aspects, the parameters characterizing the upper airway condition and/or disorder may be communicated to a system and method of preventing and/or treating an upper airway condition and/or disorder for use in generating a treatment.

In various other aspects, the system and method of preventing and/or treating an upper airway condition and/or disorder delivers at least one stimulation to modulate at least one reflex including, but not limited to, a swallowing reflex, a negative pressure reflex, or any combination thereof. The stimulation may be delivered to a reflex-related nerve, a reflex-related muscle, a reflex-related sensory receptor, and any combination thereof. The delivery of the stimulation may reduce the threshold of the reflex by enhancing the intensity of the neural signal delivered by an upper airway afferent in one aspect. In another aspect, the delivery of the stimulation may maintain the muscle tone of upper airway muscles involved in a preselected activity. In yet another aspect, the delivery of the stimulation may trigger the reflex, which may include but is not limited to a swallow reflex and a negative pressure reflex.

In these various other aspects, the stimulation may be delivered autonomously according to a predetermined schedule. In other aspect, the stimulation may be delivered in response to a stimulation signal generated using parameters characterizing the upper airway condition and/or disorder. These parameters may be received from an independent device including, but not limited to, a patient monitor device in one aspect. In another aspect, the parameters may be generated by the system and method of monitoring an upper airway condition described herein in various aspects.

In various additional aspects, the system and method of monitoring an upper airway condition and the system and method of preventing and/or treating an upper airway condition and/or disorder may be combined into a system and method for monitoring, preventing, and/or treating an upper respiratory condition and/or disorder in other additional aspects.

The systems and methods of monitoring an upper respiratory condition, systems and methods of preventing and/or treating an upper respiratory conditions and/or disorders, and combined systems and methods of monitoring, preventing and/or treating and upper respiratory condition and/or disorder are described in detail herein below.

2. Method of Monitoring an Upper Airway Condition

The method of monitoring an upper airway condition processes a neural signal obtained from an upper airway to generate an activity profile characterizing an upper airway condition. FIG. 11 is a flow chart illustrating the method 1100 in an aspect. In this aspect, at least one neural signal is obtained from an upper airway afferent such as an iSLN using a measurement device such as a nerve electrode at step 1102. The at least one neural signal may be amplified and processed using an algorithm such as a rectification and bin-integration (RBI) algorithm to obtain one or more neural activity profiles at step 1104. The one or more neural activity profiles may include information characterizing aspects of the one or more neural signals including, but not limited to, the neural signal's timing, phase, amplitude, conduction velocity, and position.

In this aspect, the one or more neural activity profiles may be compared to one or more activity criteria to associate each neural activity profile with an associated activity type at step 1106. Each activity criteria may include one or more predetermined reference values uniquely characterizing the associated activity type. For example, a reflux criterion, which typically involves a pain signal generated by a "C" type, may be characterized by a conduction velocity of less than about 2 m/s. Thus, if a neural activity profile is determined to include a conduction velocity of less than about 2 m/s during the comparison of step 1106, this neural activity profile's associated activity type would be a reflux activity type. The associated activity type for a particular neural activity profile may be further used to guide subsequent analysis of the profile.

Based on its associated activity type, each neural activity profile is processed at step 1108 to determine one or more activity states characterizing the profile. For example, for a neural activity profile associated with a reflux activity type, one or more reflux states may be obtained at step 1108 including, but not limited to: reflux timing, reflux pH, reflux location, and any combination thereof. In this aspect, the one or more activity states represent parameters that characterize and/or quantify a particular activity prior to a diagnosis of the subject.

In one aspect, the one or more activity states determined at step 1108 may be displayed and/or communicated to another device such as a patient monitor device or treatment device. In another aspect, the one or more activity states may be processed to obtain at least one condition of the subject at step 1110. In this aspect, the one or more conditions obtained at step 1110 represent a diagnosis regarding the healthy or appropriate function of the subject with respect to one or more activities. For example, if the associated activity type of a neural activity was a reflux activity type, the one or more reflux activity states may be processed to obtain one or more reflux conditions including, but not limited to, esophageal reflux, pharyngeal reflux, laryngeal reflux, and any combination thereof.

The at least one condition of the subject obtained at step 1110 may be displayed and/or communicated to another device such as a patient monitor device or treatment device in an aspect. In another aspect, the at least one condition may be assessed at step 1112 to predict a disorder. In this other aspect, the disorder may represent a broader characterization of the subject's health or physiological status. For example, if one or more reflux conditions were obtained at step 1110, a related disorder including, but not limited to GERD or acid reflex may be predicted at step 1112. In one aspect, the one or more disorders determined at step 1112 may be displayed and/or communicated to another device such as a patient monitor device or treatment device. In another aspect, the one or more disorders may be further processed to determine a treatment for the disorder by a combined method of monitoring, preventing, and/or treating an upper airway disorder as described herein below.

a. Conditions and Disorders

In various aspects, the method 1100 obtains conditions at step 1110 and predicts disorders at step 1112. A described previously, the conditions represent a diagnosis regarding the healthy or appropriate function of the subject with respect to one or more activities. Disorders, by contrast may represent a more systemic dysfunction of the subject with respect to one or more activities including, but not limited to a respiratory activity, a deglutition activity, vibration activity, a reflux activity, and any combination thereof. A more detailed description of the conditions and disorders in various aspects are provided herein below.

i. Respiratory Conditions and Disorders

In an aspect, the method 1100 may obtain one or more respiratory conditions at step 1110. Non-limiting examples of respiratory conditions include normal breathing, apnea, tachypnea, hyperpnea, hypopnea, polypnea, dyspnea, bradypnea, cough, Cheyne-Stokes respiration, Biot's respiration, ataxic respiration, Kussmaul respiration, wheezing, irregular respiration, respiratory arrest, restrictive respiration, shallow breathing, and hypoventilation.

In another aspect, the method 1100 may predict one or more disorders, including one or more respiratory disorders and/or respiratory-related disorders, at step 1112. Non-limiting examples of respiratory disorders and respiratory-related disorders include obstructive apnea, central apnea, heart failure, asthma, cardiac arrest, organ failure, metabolic acidosis, COPD, hypoventilation syndrome, laryngeal penetration, and aspiration.

Detailed descriptions of selected respiratory conditions and disorders are provided herein below.

Normal Respiration

During normal inspiration, the diaphragm and intercostal muscles contract, creating a negative pressure in the airway and drawing air into the lungs. Expiration is typically passive, resulting from relaxation of the diaphragm and intercostal muscles back to their resting position, and elastic recoil of the lungs. The amount of air flow produced by a given inspiratory pressure is influenced by resistance from the structures of the upper airway, including the soft palate, tongue, and epiglottis.

A schematic illustration of the human airway 100, in particular the upper airway 110, is provided in FIG. 1. During normal inspiration, the diaphragm and intercostal muscles 120 contract to a flattened position 122, inducing a negative pressure in the airway 100 and drawing air into the lungs 104. Expiration is typically passive, resulting from relaxation of the diaphragm and intercostal muscles 120 back to a upward domed resting position 124, and elastic recoil of the lungs 104. The amount of outward air flow through the larynx 102 produced by the change in airway 100 pressure may be influenced by resistance from the structures of the upper airway 110, including the soft palate 112, tongue 114, pharynx 116, and epiglottis 118.

Figure 2:
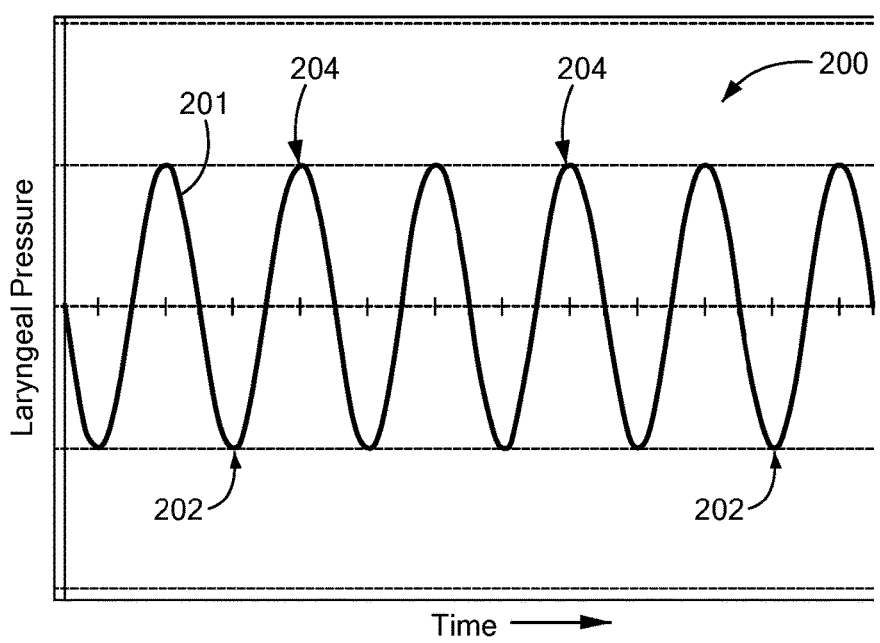
FIG. 2 is a graph of airway pressure measured at the larynx during the normal breathing process.

FIG. 2 is a graph 200 summarizing the airway pressure 201 measured at the larynx 102 (see FIG. 1) during a normal breathing process, comprising regular inspiration 202 and expiration 204 peaks of comparable amplitude and frequency. Airway pressure at the larynx 102 is perceived by mucosal mechanoreceptors that are sensitive to pressure; this airway pressure is communicated to the central nervous system via the internal branch of the superior laryngeal nerve (iSLN).

Figure 3:
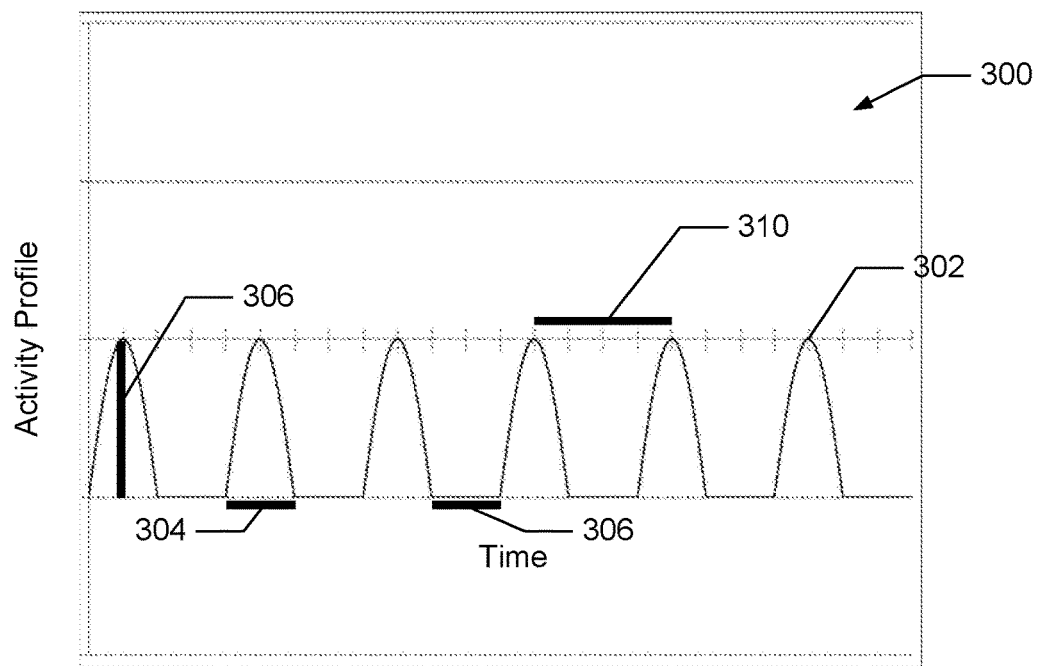
FIG. 3 is a graph of the activity profile measured during the normal breathing process.

The activity of pharyngeal afferent fibers exhibit regular bursts during normal respiration that correspond to the time and amplitude profile of negative pressure during inspiration. FIG. 3 is a graph 300 summarizing the activity profile 302 measured during the normal breathing process. The activity profile 302 exhibits a similar regularly-spaced neural activity surges with little variation in activity surge width 304, peak surge amplitude 306, time between bursts 308, and/or separation of surge peaks 310. The amplitude of these bursts in the activity profile during each breath occurs within a normal range of amplitudes which may be determined using a calibration process during normal respiration of a given subject using, for example, polysomnographic techniques. This range of amplitudes may be used to determine upper and lower thresholds for normal breath detection using the method 1100. Bursts with peaks outside of this normal range may be detected using simple fixed-level thresholds and defined as abnormal respiratory events.

Using this technique, the pattern of changing respiratory pressures, encoded on a breath-to-breath basis by bursts of activity on pharyngeal afferent nerves, may be used to identify respiratory pattern, respiratory timing, respiratory phase, and the amplitude of airway pressure.

Sleep Apnea

The principal forms of sleep apnea are: 1) obstructive sleep apnea (OSA), characterized by a physical blockage of the upper airway during sleep, 2) central sleep apnea (CSA), caused by a decreased central respiratory drive during sleep, and 3) mixed sleep apnea, which includes components of both OSA and CSA. OSA is the most common and dangerous of all sleep-related breathing disorders. While CSA is uncommon in its pure form, it is prevalent in patients with congestive heart failure, as a component of Cheyne-Stokes respiration.

The obstructive component in OSA is related to decreased pharyngeal tone as the muscles relax during sleep. During normal respiration, upper airway patency is maintained by the negative pressure reflex, which activates pharyngeal dilators in response to negative transthoracic pressure during inspiration. In apneic patients, the negative pressure reflex is insufficient to maintain patency during sleep. Here, the negative pressure created during inspiration, in tandem with gravitational force acting on the surrounding tissues is sufficient to constrict or collapse the lumen of the flaccid airway.

Figure 4:
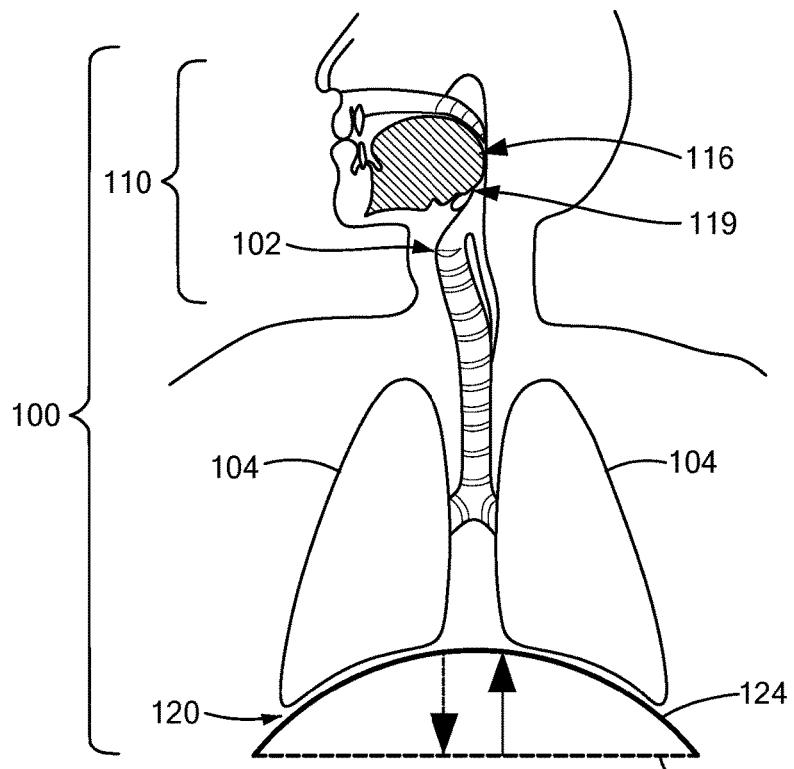
FIG. 4 is a schematic representation of the human airway relevant to upper airway pressure as measured at the larynx during an obstructive sleep apnea (OSA) event.

FIG. 4 is a schematic representation of the human airway during an OSA event. A lack of muscle tone in the upper airway 110 allows pharyngeal structures 116 to partially or completely block the lumen 119 of the airway 100, particularly when subjects sleep on their back. Respiratory drive continues during the OSA event, the diaphragm and intercostal muscles 120 contract 122, creating a negative pressure in the airway 100 that draws flaccid pharyngeal structures 116 into the airway lumen 119.

Figure 5:
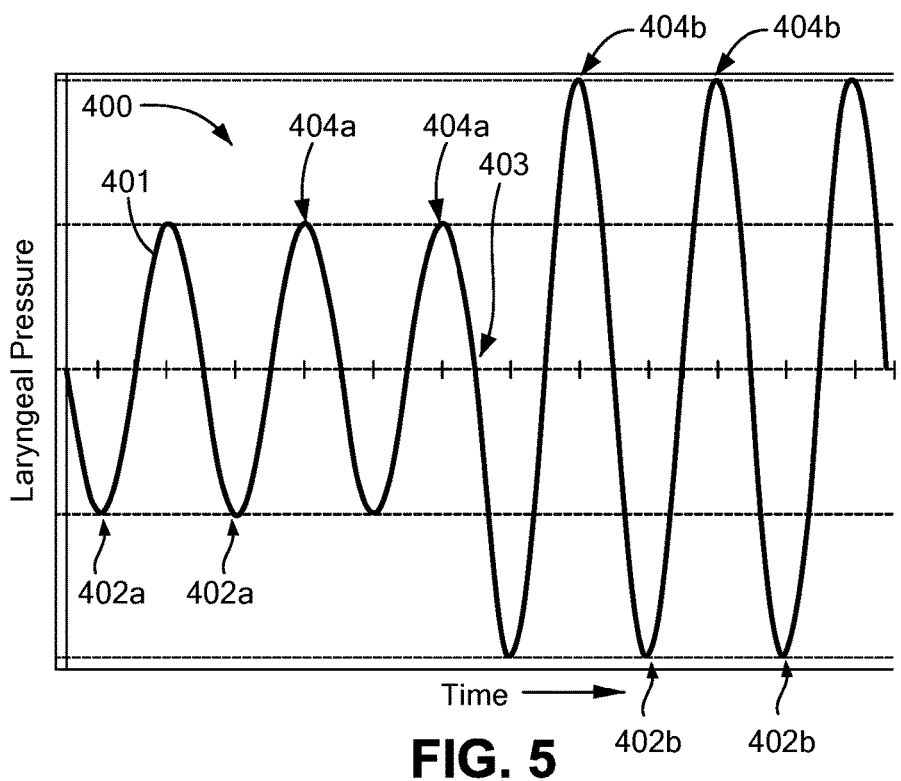
FIG. 5 is a graph of airway pressure measured at the larynx at the outset of an OSA event.

FIG. 5 is a graph 400 of airway pressure 401 measured at the larynx 102 (see FIG. 3) at the outset of an OSA event, comprising normal breathing process inspiration 402a and expiration 404a peaks before the OSA event and then inspiration 402b and expiration 404b peaks of a greater amplitude during the OSA event. This increase in the amplitude of the airway pressure 401 reflects continuing attempts on the part of the subject to breathe after airway obstruction, generating greater than normal airway pressures 401. The outset of the OSA event 403 can then be identified by the sudden increase in amplitude of the inspiration 402 and expiration 404 peaks of the airway pressure 401.

Figure 6:
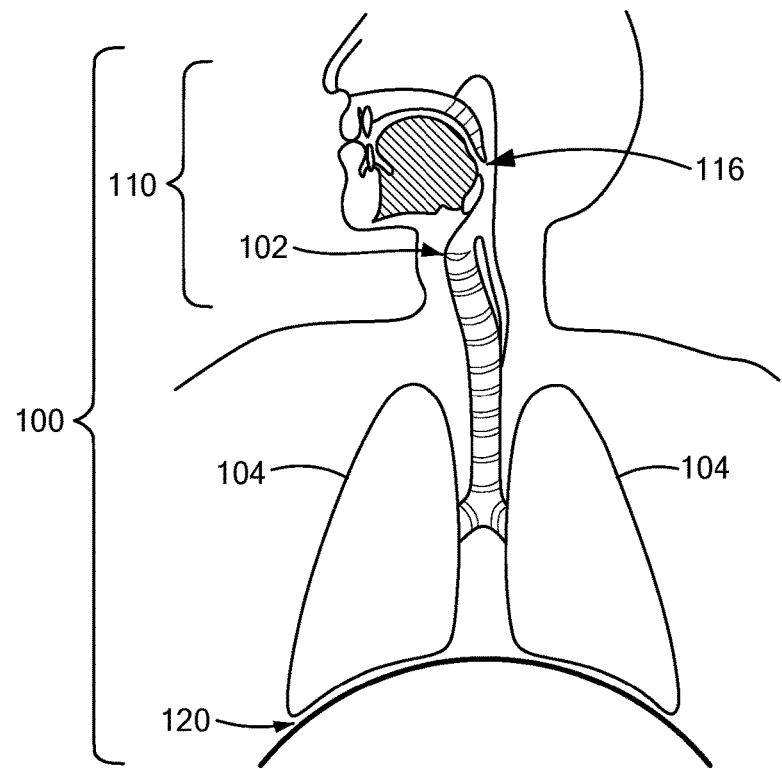
FIG. 6 is a schematic representation of the human airway relevant to upper airway pressure as measured at the larynx during a central sleep apnea (CSA) event.

A schematic representation of the human airway 100 during a CSA event is illustrated in FIG. 6. The upper airway 110 remains open, but diminished central respiratory drive reduces or eliminates diaphragm 120 movement, thereby reducing or halting air flow during the CSA event.

Figure 7:
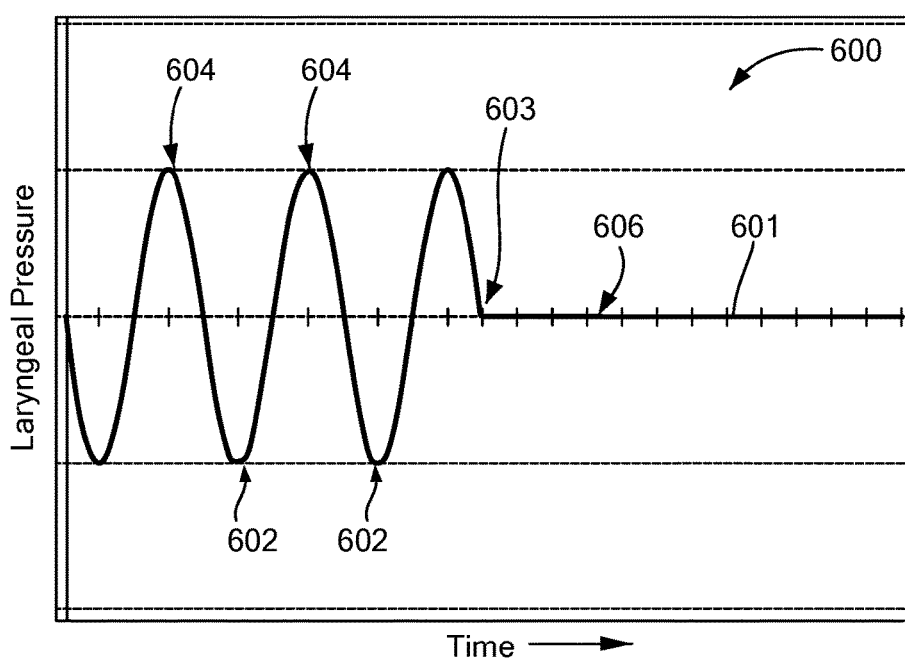
FIG. 7 is a graph of airway pressure measured at the larynx at the outset of a CSA event.

FIG. 7 is a graph 600 of airway pressure 601 measured at the larynx 102 (see FIG. 5) at the outset of a CSA event, comprising normal breathing process inspiration 602 and expiration 604 peaks before the CSA event and then an absence of, or very low amplitude, inspiration and expiration peaks 606 during the CSA event. Despite a patent upper airway 110, upper airway pressure 601 is not fully modulated after the onset of the CSA event and diminution of diaphragm movement. The outset of the CSA event 603 can then be identified by the sudden drop 606 in the amplitude of the inspiration 602 and expiration 604 peaks of the airway pressure 601.

ii. Deglutition Conditions and Disorders

In an aspect, the method 1100 may obtain one or more deglutition conditions at step 1110. Non-limiting examples of deglutition conditions include presence of unswallowed bolus, occurrence of swallow, occurrence of dysphagic swallow, and presence of acid reflux.

In another aspect, the method 1100 may predict one or more disorders, including one or more deglutition disorders and/or deglutition-related disorders, at step 1112. Non-limiting examples of deglutition disorders and deglutition-related disorders include obstructive apnea, dysphagia, presence of unswallowed bolus, and aspiration.

Detailed descriptions of selected deglutition conditions and disorders are provided herein below.

Normal Swallowing

Figure 8:
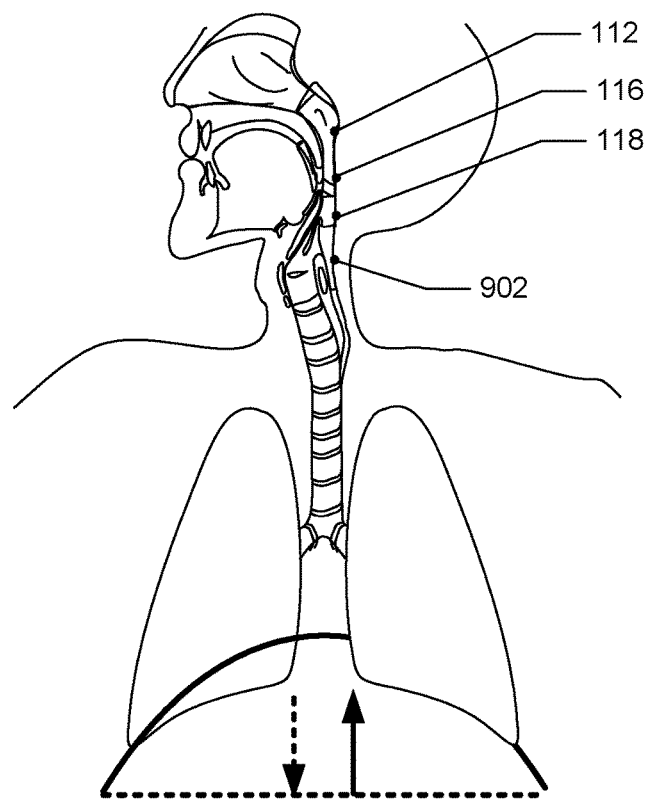
FIG. 8 is a schematic diagram illustrating the cranial-caudal distribution of structures relevant to a deglutition activity.

Deglutition or swallowing is a stereotyped reflex that exhibits a consistent pattern of activation of 50 muscles throughout the upper airway. This sequence acts to propel food and fluid caudally at speeds of about 1M/sec with the pharyngeal stage of the swallow taking about 1 sec to complete. FIG. 8 is a schematic illustration showing the upper airway structures relevant to deglutition. The swallow sequence is essentially a progressive anterior-to-posterior wave of pharyngeal contact that acts to squeeze the bolus from the soft palate 112 posteriorly to the pharynx 116, further posteriorly to the epiglottis 118 and ultimately toward the esophagus 902 like a tube of toothpaste while simultaneously protecting the airway from entry of material.

The resulting stereotypical pattern of neural activity across the pharyngeal touch and pressure sensitive afferents would be apparent both within individual afferent fibers and across populations of fibers. A schematic diagram showing the anterior-to-posterior activation pattern in the activity profile is provided as FIG. 9. The actual pattern of the activity profile is influenced by the pattern of mechanical contact and pressure on a given mucosal receptor and by the adaptation properties of the afferent fibers.

Figure 9:
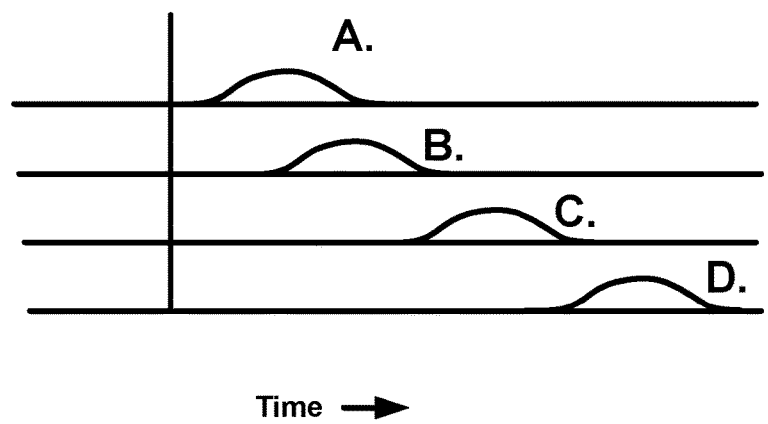
FIG. 9 is a series of graphs showing the anterior-posterior pattern of activity profiles measured during a normal deglutition condition; the graph designated A is an activity profile of the soft palette; the graph designated B is an activity profile of the pharynx; the graph designated C is an activity profile of the epiglottis; and the graph designated D is an activity profile of the esophagus.
Figure 10:
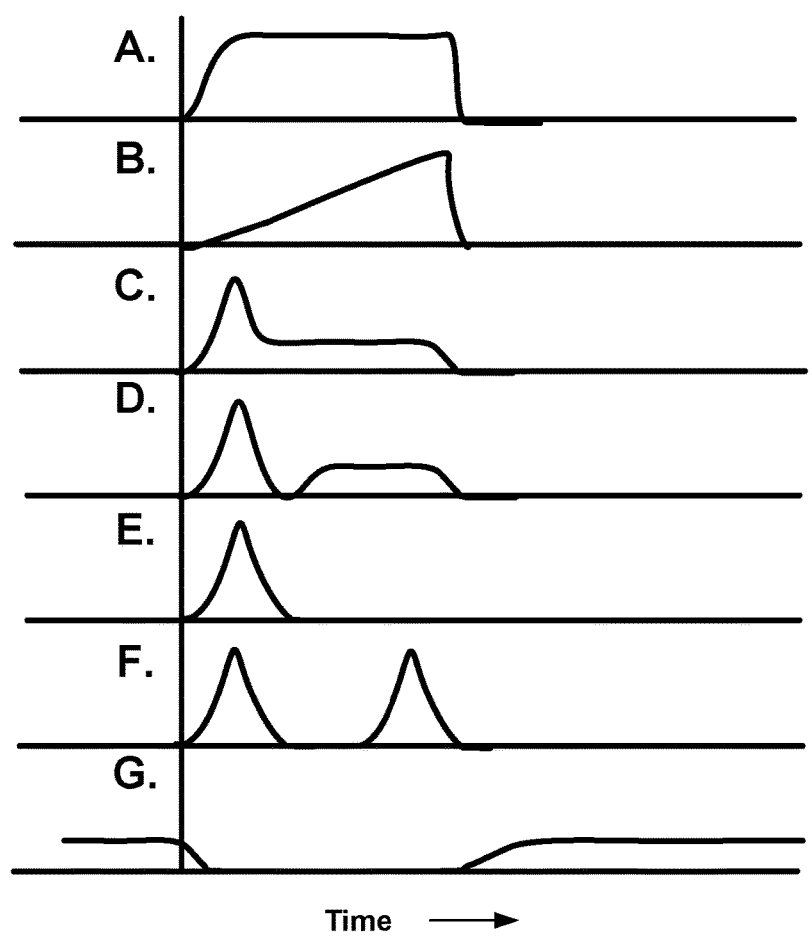
FIG. 10 is a series of graphs schematically illustrating the activity profiles of a variety of neural signals during a reflux condition; the graph designated A is an activity profile characterizing a tonic neural response; the graph designated B is an activity profile characterizing a build-up neural response; the graph designated C is an activity profile characterizing an on-sustained neural response; the graph designated D is an activity profile characterizing a pauser neural response; the graph designated E is an activity profile characterizing an onset neural response; the graph designated F is an activity profile characterizing an on-off neural response; and the graph designated G is an activity profile characterizing a tonically-inhibited neural response.

For example, the receptors in pharyngeal surface of the soft palate 112 would experience a stereotyped increasing pressure profile as the palate lifts to seal the nasal cavity from the bolus, followed by a stereotyped decreasing pressure profile as the bolus passes, as illustrated in FIG. 9, graph A. Depending on the rate of adaptation within an individual fiber, this may create a variety of activity profiles. FIG. 10 is a graph summarizing a variety of activity profiles associated with different types of individual fibers. In various aspects, the activity profile may be a "tonic" profile (FIG. 10, graph A), a "buildup" profile (FIG. 10, graph B) characterizing relatively slowly adapting receptors, an "on-sustained" profile (FIG. 10, graph C), a "pauser" profile (FIG. 10, graph D), an "onset" profile (FIG. 10, graph E), or an "on-off" profile (FIG. 10, graph F) characterizing progressively more rapidly adapting receptors. Spontaneously active fibers may exhibit, for example, a "tonically-inhibited" activity profile during applied pressure, as illustrated schematically in FIG. 10, graph G.

The area of and location of contact between the soft palate and posterior pharyngeal wall may also exhibit a stereotyped pattern during swallow, creating a spatial activity pattern across a population of fibers, in addition to the temporal activity pattern within individual fibers. On a larger spatial scale, the anterior to posterior pharyngeal contact pattern would act to create a stereotypical spatial activity pattern, with most anterior fibers being activated at the beginning of the swallow sequence and the most posterior fibers being activated about a second later, as illustrated schematically in FIG. 9.

In one aspect, the neural signals recorded from iSLN receptors are relevant to the gastrointestinal (GI) condition of a subject. The iSLN mechanoreceptors normally indicate bolus contact and trigger a swallow sequence.

Dysphagia, as referred to herein, refers to the medical symptom of difficulty in swallowing, and is frequently diagnosed in subjects also presenting with sleep apnea. Subjects may have a great deal of difficulty in controlling even saliva in the mouth, or difficulty in initiating a swallow, or a cough. Dysphagia thus represents a further example of a high medical risk due to impaired pharyngeal motor control.

The activity profile within and between individual fibers and fiber populations may be determined using a calibration process during normal deglutition of a given subject, created for example, during volitional "dry" swallowing or in the presence of an administered bolus of food or fluid. The activity profile for dysphagic swallow and/or presence of an unswallowed bolus may be similarly determined. The range of normal temporal and/or spatial activity patterns observed during the calibration process can computed and be used to set for example matched-filter templates and upper and lower thresholds for detection of normal swallow and dysphagic swallow. Peaks within this range may be detected using simple fixed-level thresholds and used to assign a deglutition activity as the associated activity type of the neural activity profile.

iii. Vibration Conditions

In an aspect, the method 1100 may obtain one or more vibration conditions at step 1110. Non-limiting examples of vibration conditions include snoring, stridor, wheezing and vocalization. In another aspect, the method 1100 may predict one or more disorders, including one or more vibration disorders and/or vibration-related disorders, at step 1112.

Detailed descriptions of selected deglutition conditions and disorders are provided herein below.

Snoring is caused by the vibration of flaccid pharyngeal tissues during sleep, and snoring may an early indicator of the development of an obstructive sleep apnea (OSA). The walls of the mucosa are known to contain specialized mechanoreceptors that are sensitive to vibration. Three different vibration receptor types are known, each responding best to vibration over a different range of frequencies. Merkel disks, for example, respond best to vibrations from about 5-15 Hz, while Meissner corpuscles have a best frequency of about 50 Hz. Both of these receptors types have been histologically identified in the airway mucosa. A third class of mucosal mechanoreceptors is known to respond to vibration up to 300 Hz, with a best frequency of about 150 Hz; these response properties correspond to those known for Pacinian corpuscle receptors.

Figure 11A:
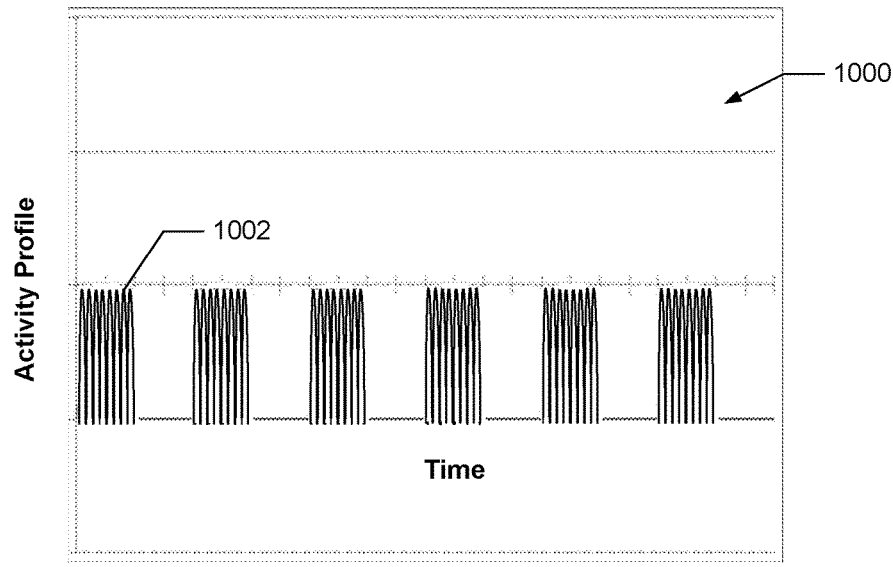
FIG. 11A is a graph of an activity profile measured during a vibration condition.
Figure 11B:
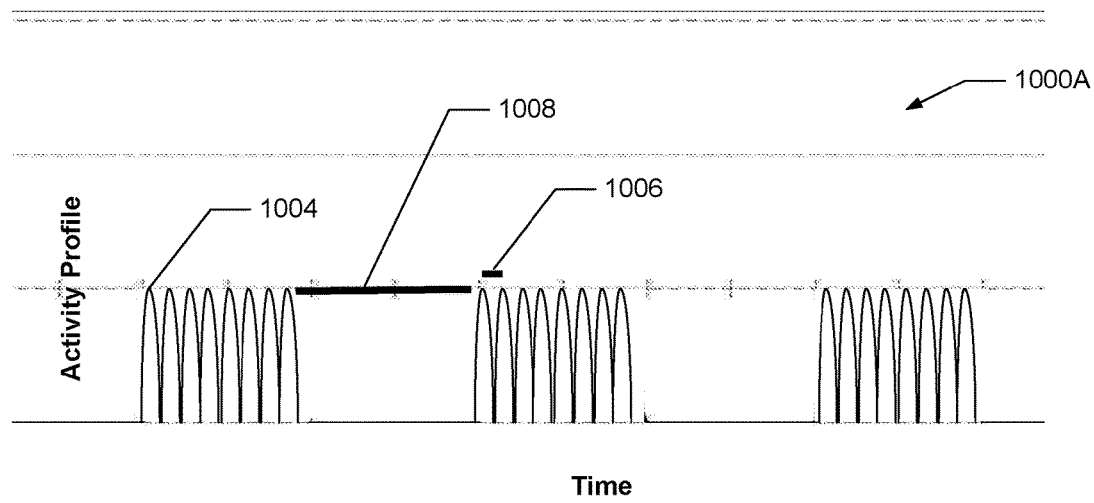
FIG. 11B is the activity profile measured during a vibration condition on a zoomed-in time scale.
Figure 12:
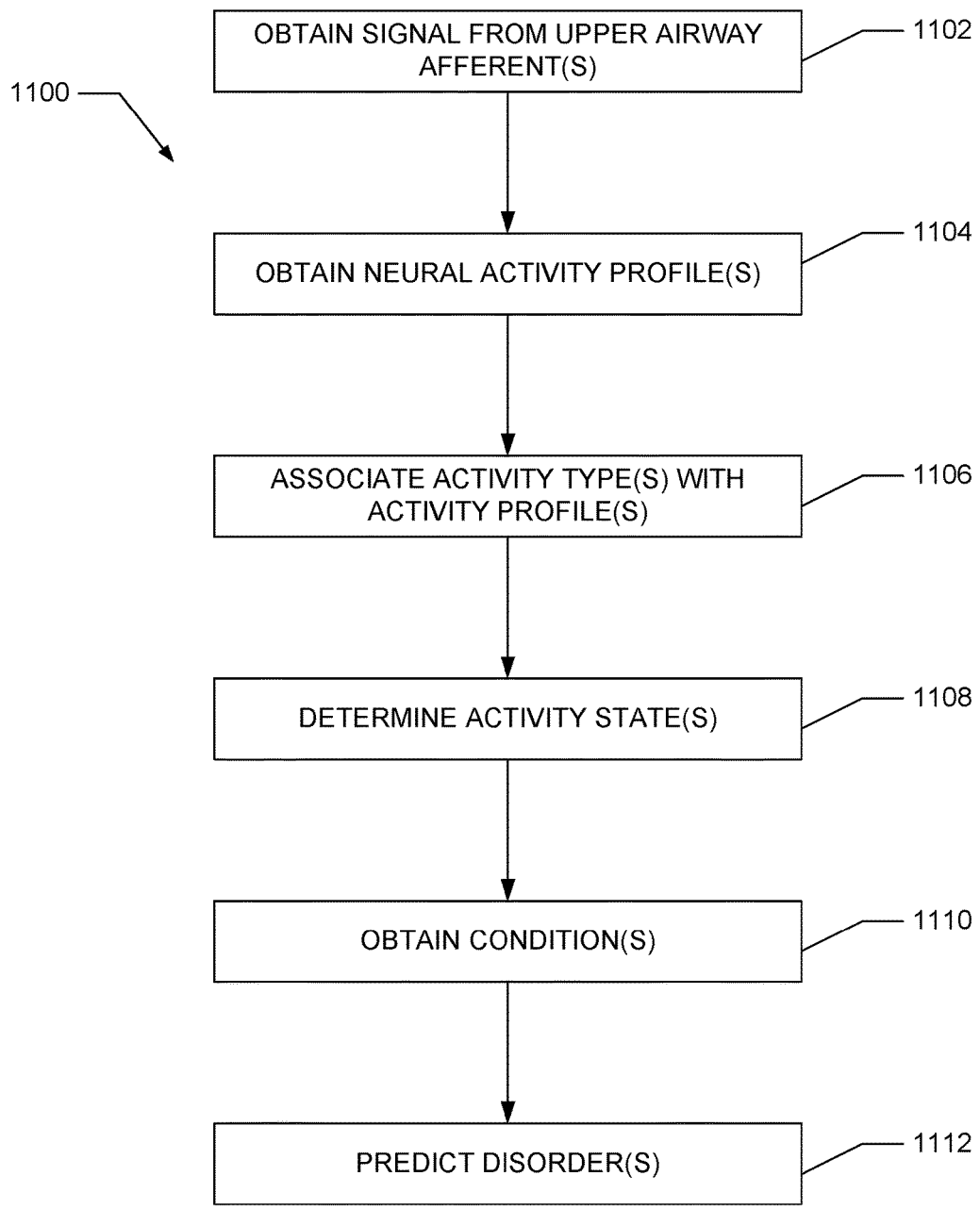
FIG. 12 is a schematic diagram of a method for monitoring an upper airway condition.

FIG. 11A is graph 1000 illustrated schematically an activity profile 1002 of a vibration-sensitive mechanoreceptor. As illustrated in graph 1000A, the activity profile 1002 shown at a zoomed in time scale, these vibration-sensitive mechanoreceptors may exhibit phase-locked activity at the frequency of the vibration, thereby encoding the stimulus frequency by a single action potential 1004 on every cycle, or at higher frequencies, at integer multiples of the interval between cycles. This produces a characteristic interspike interval 1006 for these phase locking fibers that matches or is a multiple of the period of the vibration. Further, the envelope of the activity profile during pharyngeal vibration may exhibit amplitude modulations as a result of phase locking, as illustrated by the graph. The interspike interval 1006, amplitude modulation frequency, vector strength and modulation depth occurring at a given vibration frequency may be determined using a calibration process during normal pharyngeal vibration of a given subject, created for example, by volitional vocalization, snoring, or wheezing. Artificially induced vibration using, for example, a piezoelectric vibrator placed on the skin over the pharynx may also be used. The range of interspike intervals, amplitude modulation frequencies, vector strengths and modulation depths observed during the calibration process can computed and be used to set upper and lower thresholds for vibration detection. Peaks within this range can be detected using simple fixed-level thresholds and defined as vibration events.

Using these techniques, the pattern of pharyngeal vibration, encoded by characteristic interspike intervals and/or amplitude modulation of the activity profile of pharyngeal afferent nerves, can be used to identify vibration pattern, vibration timing, vibration phase, and the amplitude of vibration.

Snoring is an upper airway condition that is characterized by vibration of the pharyngeal walls, tongue base, soft palate, and tonsils. It has been discovered that the principal frequency range of human snoring occupies a spectrum from 40-300 Hz with a peak spectral power at about 100 Hz. The frequency spectrum of snoring vibration activity is well-matched to the frequency range of pharyngeal vibration sensitive mechanoreceptors and makes monitoring of pharyngeal afferents a particularly well-suited method for snoring detection.

Specific airway structures are known to vibrate at characteristic frequencies, for example, the tonsils and soft palate vibrate at about 170 and 140 Hz, respectively. This characteristic may be used to pinpoint the structural source of snoring by monitoring pharyngeal vibration receptors. If multiple upper airway afferents and/or multiple fibers within a single nerve are monitored, the location of the source of pharyngeal vibration may also be pinpointed based on the receptive fields of active afferent fibers, either by comparing activity across multiple nerves, or by comparing activity across fibers within a single nerve.

iv. Reflux Conditions

In an aspect, the method 1100 may obtain one or more reflux conditions at step 1110. Non-limiting examples of reflux conditions include esophageal reflux, pharyngeal reflux, and laryngeal reflux.

In another aspect, the method 1100 may predict one or more disorders, including one or more reflux disorders and/or reflux-related disorders, at step 1112. Non-limiting examples of reflux disorders and reflux-related disorders from esophageal reflux, laryngeal reflux, acid reflux, and GERD.

Detailed descriptions of selected reflux conditions and disorders are provided herein below.

Gastroesophageal reflux disease (GERD), gastric reflux disease, or acid reflux disease is a chronic symptom of mucosal damage caused by stomach acid coming up from the stomach into the esophagus. GERD may be divided into esophageal and extraesophageal syndromes. Acid reflux allowed by a transient relaxation of the lower esophageal sphincter that allows acid to pass into esophagus. Once in the esophagus, gastric acid can travel along the length of the esophagus, reaching or passing the level of the upper esophageal sphincter. Extraesophageal symptoms are caused by the entry of gastric juices in the larynx and pharynx through the upper esophageal sphincter. Laryngeal and pharyngeal symptoms are also known as laryngopharyngeal reflux (LPR) or extraesophageal reflux disease (EERD). Extraesophageal symptoms include dysphagia, voice disorders, asthma, hoarseness, laryngitis, chronic cough, pain, vocal fold nodules, and unstable voice during speaking or singing.

The mucosa of the upper airway is known to contain afferent fibers of different diameters and conduction velocities. In cutaneous nerves, there exist three populations of afferent fibers, each population having a characteristic signal conduction velocity. "Aβ" type fibers have the fastest signal conduction velocity and typically conduct action potentials along afferent fibers at a rate ranging from about 35 m/s to about 75 m/s. "Aδ" type fibers have an intermediate signal conduction velocity and typically conduct action potentials along afferent fibers at a rate ranging from about 5 m/s to about 30 m/s. "C" fibers have the slowest signal conduction velocity and typically conduct action potentials along afferent fibers at a rate ranging from about 0.5 m/s to about 2 m/s.

It is known that the neural activity of mucosal receptors sensitive to low pH (acidic) conditions receptors typically involved in perceiving reflux conditions is carried by the slow-conducting "C" type fibers. It was discovered that a neural activity profile characterizing reflux conditions could be isolated from a reading from an upper airway afferent that included superimposed activity profiles characterizing other conditions by assessing the conduction velocity of the neural signals within the reading.

Figure 17:
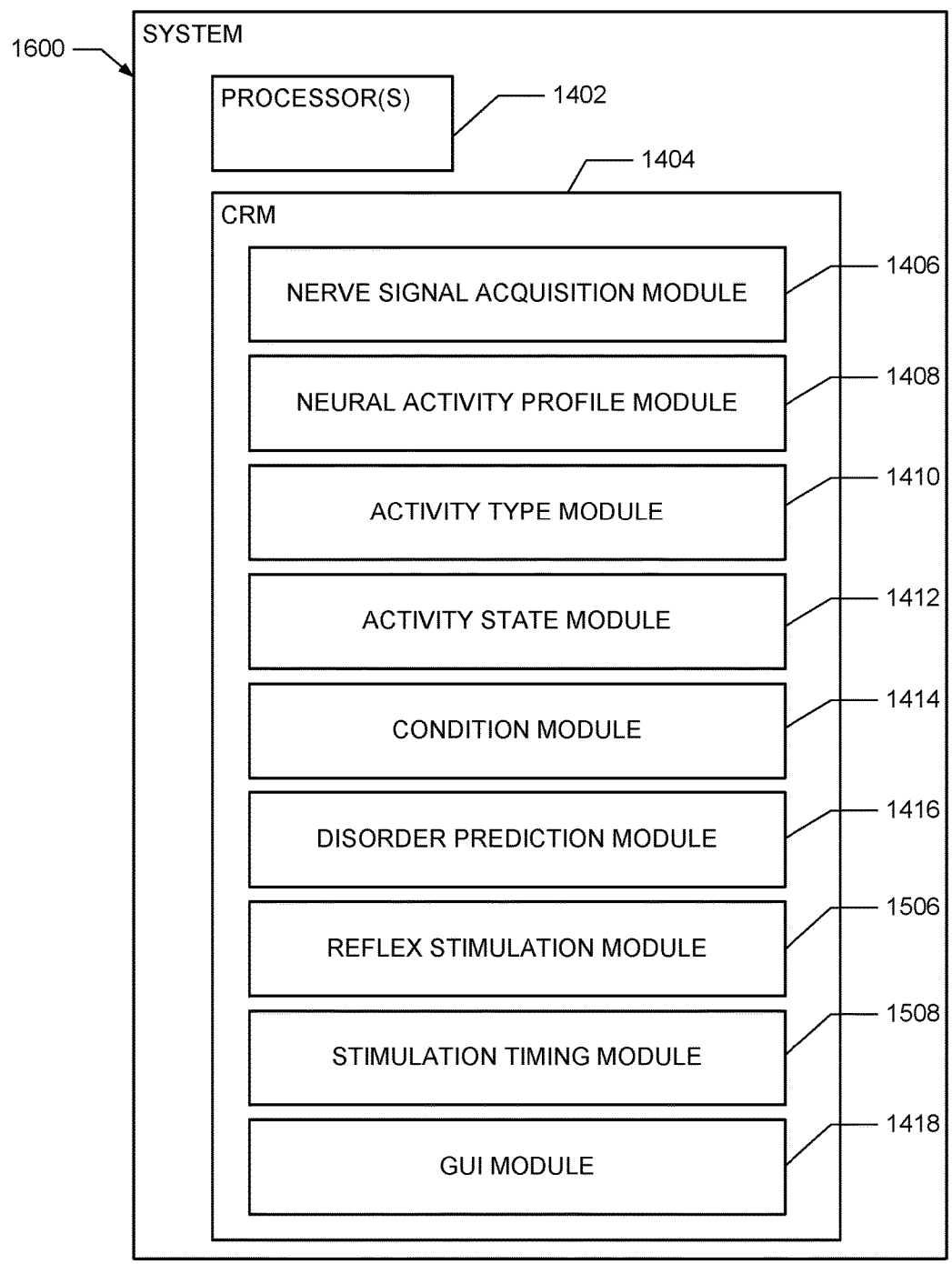
FIG. 17 is schematic diagram of a combined system for monitoring, preventing, and/or treating an upper airway condition.
Figure 18:
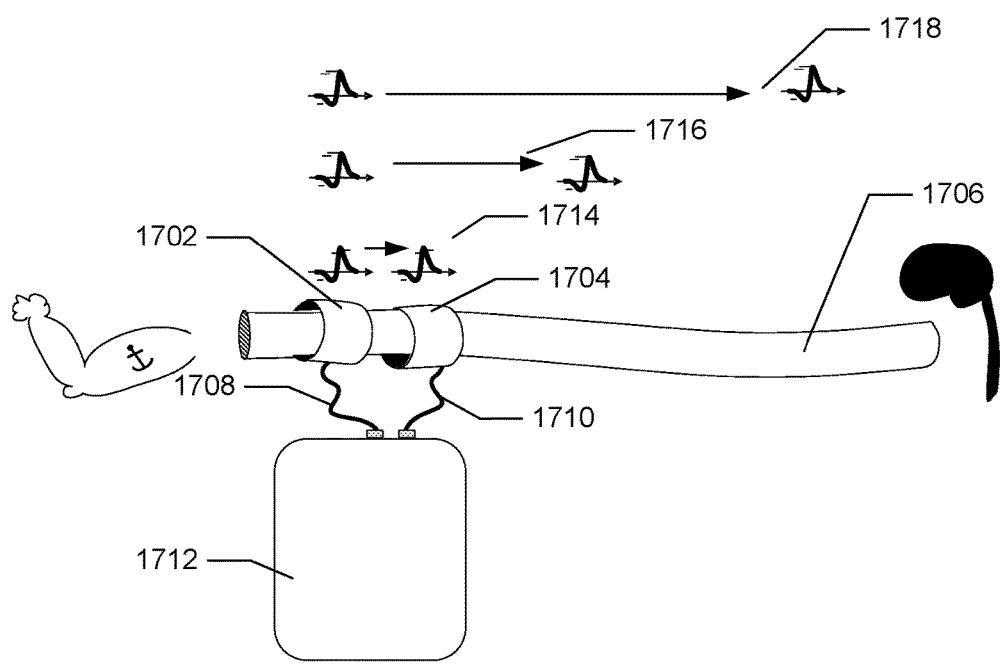
FIG. 18 is a schematic illustration of a method of isolating neural signals associated with the activity of "C" type fibers.

To isolate the "C" type fiber activity from superimposed activity of "Aβ" type fibers and "Aδ" type fibers, the activity of these three populations of nerve fibers can be differentiated using techniques based on each fiber's known signal conduction velocity. A schematic illustration of this isolation technique is shown in FIG. 17. In this technique, a peripheral recording device 1702 and a central recording device 1704 are spaced a known separation distance along the length of a given set of fibers within an afferent nerve 1706 and used to record two separate neural signals 1708 and 1710, respectively.

For example, as illustrated in FIG. 17, the recording devices 1702 and 1704 may be spaced about 1 mm apart along the length of the nerve and thus record the activity from the same set of nerve fibers at two different points along their length. In the signal processing circuit 1712, a 1 ms delay may be introduced in the signal 1708 from the peripheral recording device 1702 which is then summed with the neural signal 1710 obtained from the central recording device 1704. In this example, the "C" fiber activity covers the distance between the electrodes in about 1 ms, and thus the signals 1708 and 1710 from the recording devices 1702 and 1704 overlap in time and are added together, as schematically illustrated in graph 1714. However, the signals associated with activity from Aβ type fibers and Aδ type fibers have moved well past the central recording device 1704 during the 1 ms delay as illustrated in graphs 1716 and 1718, respectively. As a result, the portion of the signals 1708 and 1712 associated with activity from Aβ type fibers and Aδ type fibers are not added together. By setting a high threshold on the output of the circuit, the activity of only the combined "C" fiber signals may be isolated. Using a similar circuit to that illustrated in FIG. 17, the activity of acid-sensitive "C" fibers may be separated from the activity of more rapidly conducting mechanoreceptors in upper airway afferents in one aspect.

The activity profile of acid-sensitive "C" fibers may then be determined using a calibration process during acid reflux of a given subject, created for example during a normally occurring acid reflux, or created by artificial application of a low pH fluid to the pharynx. The range of normal temporal and/or spatial activity patterns observed during the calibration process may computed and be used to set, for example, upper and lower thresholds for detection of reflux in the airway in an aspect. Peaks within this range may be detected using simple fixed-level thresholds and the activity profile may be associated with a reflux activity type in another aspect. The temporal and spatial activity profiles during naturally occurring or artificial reflux conditions may also be determined in an additional aspect.

b. Neural Signals

In various aspects, the method obtains neural signals from upper airway afferents in order to monitor a condition and/or a disorder including, but not limited to a respiratory condition, a deglutition condition, a reflux condition, and a vibration condition. A detailed description of upper airway afferents suitable for use in the method is provided herein below.

i. Upper Airway Afferents

In an aspect, the upper airway afferents include nerves associated with mucosal sensory receptors situated throughout the upper airway of the subject. The neural signals produced by these mucosal sensory receptors provide a rich source of information to identify and characterize a variety of upper airway conditions and disorders, as described herein previously. Non-limiting examples of upper airway afferents include pharyngeal afferents, laryngeal afferents, oral cavity afferents and nasal cavity afferents.

Pharyngeal afferents are known to transmit information from sensory receptors in the mucosa lining the upper airway to the brain. As used herein, pharyngeal afferents innervating additional areas of the upper airway, such as the larynx, are included in the term "pharyngeal afferents". Non-limiting examples of pharyngeal afferent include the comprising iSLN branch of vagus nerve, pharyngeal branch of vagus nerve, pharyngeal branch of glossopharyngeal nerve, tonsilar branch of glossopharyngeal nerve, lingual branch of glossopharyngeal nerve, intermediate nerve, palantine nerve, greater petrosal nerve, any branch of facial nerve, pterygopalatine nerve of trigeminal nerve, and any combination thereof. Various aspects of the methods described herein are intended to include both the pharyngeal and extrapharyngeal sensory receptor transmission functions. For example, the iSLN innervates vocal folds in the larynx as well as mucosal sensory endings in the pharynx.

These mucosal receptors may be sensitive to stimuli including, but not limited to airway pressure characterizing respiratory conditions such as apnea, contact with food or fluid characterizing deglutitation conditions such as dysphagia, vibrations characterizing vibration conditions such as snoring, and pH characterizing reflux conditions. Non-limiting examples of additional neural signals carried by upper airway afferents include chemoreceptors modulated by pH, taste receptors modulated by various chemical compounds, thermoreceptors modulated by temperature or airflow, or noiceptors modulated by polymodal pain, It has been discovered that the measurements of neural activity, including but not limited to the electroneurogram (ENG) of pharyngeal afferent nerves is modulated by changes in these variables. This relationship can be demonstrated by obtaining one or more neural activity profiles of the pharyngeal afferent nerve that is indicative of the amplitude and timing of the ENG signal in one aspect. The neural activity profile may be calculated for example by applying a rectification and bin-integration (RBI) algorithm to an amplified pharyngeal afferent signal and used to detect and/or monitor an upper airway condition and/or disorder. Neural response characteristics such as the number of elicited spikes, the interval between spikes, and the temporal spike pattern in response to continued stimulation may vary with stimulus variables such as intensity and duration.

Each sensory nerve fiber responds to adequate stimuli applied within their "receptive field", defined herein as the specific area of the sensory epithelium innervated by a sensory nerve fiber. In an aspect, the spatial extent of sensory stimuli may be determined by comparing neural response between fibers with different receptive fields, which are often organized in a topographic map. For example, spinal nerves are organized segmentally and typically innervate specific regions of skin (dermatomes) in an organized fashion, with cervical nerves innervating the upper body and sacral nerves innervating the lower body. On a finer scale, individual spinal nerves can also be somatotopically organized, with fibers from receptors close to one another within a dermatome grouped together into bundles called fascicles within the nerve. In an aspect, the receptive field characteristics associated with one or more sensory fibers within an upper airway afferent may be used to determine the spatial extent, distribution, patterning, or any other spatially-related characteristic of a stimulus associated with an upper airway condition and/or disorder monitored using neural signals from one or more upper airway afferents.

Various aspects of the method are designed to monitor and interpret respiratory, reflux, vibration, and/or deglutitation conditions based on the neural signal characteristics including, but not limited to a firing pattern, an active fiber population, a signal conduction speed, and any combination thereof in pharyngeal afferent nerves. Specifically, these the neural signal may be compared to previously analyzed responses to calibration stimuli in order to detect pharyngeal disorders such as apnea, snoring, dysphagia or GERD, as described previously herein.

In one aspect, the method may obtain one or more neural signals from the iSLN. In other aspects, the method may obtain one or more neural signals from other pharyngeal afferents including, but not limited to trigeminal nerve afferents, facial nerve afferents associated with the from the oropharynx or nasopharynx cavity to monitor respiratory conditions and/or disorders, and glossopharyngeal afferents to monitor deglutitation conditions including, but not limited to the introduction of a bolus into the oropharynx and/or hypopharynx.

i. Upper Airway Efferents and Muscles

In other aspects, upper airway conditions and/or disorders may also be monitored by obtaining neural signals from nerves carrying efferent signals to muscles of the upper airway, diaphragm, or intercostal muscles, or by monitoring the activity of these respiratory muscles themselves, alone, or in some combination with other nerves or muscles modulated by respiratory activity.

ii. Neural Signal Measurement Devices

In various aspects, any known device capable of detecting and recording neural signals from nerves including, but not limited to, upper airway afferents may be used to obtain the neural signals used to obtain the at least one neural activity profile in the method. Non-limiting examples of suitable neural signal measurement devices include electrical sensors such as nerve cuffs; optical sensors such as optic fibers used in combination with voltage or current sensitive dyes injected into the nerve to be monitored; biological sensors; and mechanical sensors. In various aspects, any known method of recording peripheral nerve activity, such as percutaneous microneurography or optical recording of nerve activity based on voltage sensitive dyes may be used without limitation. In a different aspect, the size of the neural signal measurement devices may have a form factor ranging from about the size of a pacemaker to about the size of a cell phone application.

By way of non-limiting example, an electroneurogram (ENG) of pharyngeal afferents may be monitored recording electrodes placed in, around, or near the nerve. In one aspect, a "cuff" electrode may be situated around the nerve to record the aggregate activity of all nerve fibers in the vicinity of a single recording site. In another aspect, electrode designs and signal processing techniques may facilitate the selective recording of neural signals from smaller groups of nerve fibers ("multi units"), recording from individual nerve fibers ("single units"), discriminating the direction of an action potential propagation to differentiate between motor nerve fiber activity and sensory nerve fiber activity, and/or isolating a subset of neural signals based on the signal conduction velocity (isolating nerve fibers with a specific diameter).

It will be appreciated that multiple recording electrodes may be used, depending in the application and anatomical location to be monitored, in order to simultaneously or sequentially monitor multiple signal sources. The recording electrode may also target other nerves carrying afferent signals from peripheral receptors that exhibit modulations of bioelectric potentials correlated with upper airway conditions. Non-limiting examples of receptors that may be monitored to characterize an upper airway condition respiratory condition include: mechanoreceptors sensitive to negative airway pressure, positive airway pressure, stretch, position, shear or slip, vibration, texture, touch, touch and pressure, muscle stretch, muscle "drive", air flow, blood pressure or osmolarity; chemoreceptors sensitive to $CO_2$, $O_2$, or pH; thermoreceptors sensitive to temperature or airflow; nociceptors sensitive to polymodal pain, or any combination thereof. In one aspect, the method may include at least one electrode sensitive to at least one upper airway characteristic including, but not limited to upper airway pressure, upper airway stretch, and upper airway temperature, or alternatively may include multiple electrodes sensitive to a combination of the upper airway characteristics.

In another aspect, the monitoring of an upper airway condition may include monitoring the upper airway-related activity of other nerves, or monitoring other physical indicators of upper airway state, including, but not limited to airway pressure, muscle activity or airway flow as described in further detail herein below. The monitoring in this aspect may be achieved using any means capable of detecting a physical signal and transducing the signal to an electrical signal suitable for analysis. For example, various physical indicators of respiration and respiratory state are amenable to detection and monitoring, including but not limited to airway pressure, air flow, muscle stretch, muscle position, muscle "drive", blood pressure, blood osmolarity, blood gas ($CO_2$ and $O_2$), heart rate, and blood pH. Techniques and apparatus for detecting and monitoring such physical indicators are well known and widely available and may be used alone or in combination, and are generally coupled to leads that transmit data to analytic components. For example, multiple electrodes may be placed in or on the body to measure, for example, breathing rate and heart rate. Changes in abdominal or thoracic circumference related to respiration can be measured using belt-based systems with sensors based on piezoelectric or impedance sensors. An oximeter can be used to detect and monitor blood oxygen levels in the blood. A blood pressure cuff or arterial catheter may also be used, to detect and monitor blood pressure. EMG leads can be used to detect breathing muscle activity. A manometer can be placed in the nasal cavity to detect airway pressure.

In other additional aspects, upper airway conditions may be monitored using any of a number of anatomical elements involved in respiration and control of respiration. For example, respiratory activity may also be monitored from nerves carrying efferent signals to muscles of the upper airway, diaphragm, or intercostal muscles, or by monitoring the activity of these respiratory muscles themselves, alone, or in some combination with other nerves or muscles modulated by respiratory activity.

c. Neural Activity Profiles

In various aspect of the method, one or more neural activity profiles characterizing aspects of the neural signals including, but not limited to, neural signal timing, neural signal amplitude, neural signal phase, neural signal position, neural signal conduction velocity, and any combination thereof, may be obtained using one or more signal processing techniques described herein above in connection with the upper airway conditions. Additional signal processing techniques are described in detail herein below.

i. Signal Processing

In various aspects, the neural signals obtained from the one or more upper airway afferents are processed to obtain at least one neural activity profile. In one aspect, the neural signals obtained from the one or more upper airway afferents may be conditioned by any known method including but not limited to amplification prior to performing any additional signal processing. In another aspect, the neural activity profile may be obtained by applying a rectification and bin-integration (RBI) algorithm to the conditioned (i.e. amplified) neural signals.

By way of non-limiting example, a pressure in the upper airway may be monitored by obtaining an electroneurogram (ENG) of the iSLN, which is correlated with pressure in the upper airway. An index of respiratory activity (IRA) may be calculated by applying a rectification and bin-integration (RBI) algorithm to the amplified iSLN neural signal. The amplitude of peaks in the IRA during each breath that occur within a normal range of amplitudes may be determined using a calibration process during normal respiration of a given subject using, for example, polysomnographic techniques. This range of "normal" amplitudes can be used to define upper and lower thresholds for the detection of one or more respiratory conditions. Peak amplitudes falling 0 outside of this normal range may be detected using simple fixed-level thresholds and defined as a respiratory conditions. The defined upper and lower thresholds may further be used to classify, in real-time, a detected apneic event as being either an OSA event or a CSA event, as described herein previously.

The signal conditioning may be implemented by any known signal processing circuitry including, but not limited to, a signal amplifier and a rectifier circuit. Non-limiting examples of suitable amplifiers and rectifier circuits are disclosed in U.S. Patent Application Publication No. 2006/0189881 entitled "IMPLANTABLE SIGNAL AMPLIFYING CIRCUIT FOR ELECTRONEUROGRAPHIC RECORDING", published Aug. 24, 2006, by Baru Fassio and U.S. Pat. No. 7,282,980 entitled "PRECISION RECTIFIER CIRCUIT FOR HIGH-DENSITY, LOW-POWER IMPLANTABLE MEDICAL DEVICE", issued Oct. 16, 2007, to Baru Fassio, both of which are incorporated by reference in their entirety.

It is to be understood that the activity profile may be calculated by applying a rectification and bin-integration (RBI) algorithm to the amplified pharyngeal afferent signal in one aspect, other signal processing algorithms may also be applied to calculate the activity profile including, but not limited to: high pass filter, low pass filter, bandpass filter, notch filter, FIR filter, IIR filter, smoothing, moving average, Wiener (optimal) filter, matched filter, rectification, bin-integration, multichannel noise reduction, principal components analysis, independent components analysis, wavelet analysis, Fourier transformation, matched filtering, variance/variance ratio calculations, signal-to-noise ratios, cross-correlation, auto-correlation, Rayleigh statistic, and any combination thereof. In another aspect, the raw pharyngeal afferent ENG waveform may also be used directly. Activity profiles based on neural network analyses, cluster analysis in multidimensional feature space, cluster cutting using k-means, Bayesian expectation-maximization, likelihood ratios, closest centers, or manual cluster cutting methods may also be used in various aspects.

It is to be also understood that an activity profile could be computed from any number of other pharyngeal afferent ENG signal features that vary with pharyngeal state such as event or waveform timing, interval, amplitude, duration, rise time, fall time, slope, presence, absence, pattern, 1st derivative, 2nd derivative, 3rd derivative, root mean square amplitude, peak-to-peak amplitude, variance, statistical probability or probability relative to baseline or running average.

It is also to be understood that detection of pharyngeal events in the activity profile using methods other than fixed-level thresholding may be used, for example noise-tracking or other adaptive thresholds, energy or non-linear energy thresholds, or any variety of other detection operations on the raw or processed data.

In other additional aspects, the signal processing of the one or more neural signals may further include analyzing a timing sequence of two or more activity patterns, wherein each of the two or more activity patterns is obtained from different upper airway afferents. In yet other additional aspects, the signal processing of the one or more neural signals may further include assessing the spatial extent or spatial location of the one or more detected neural signals using information characterizing the receptive fields associated with the one or more detected neural signals.

d. Activity Types

In various aspects, the at least one neural activity profiles may be compared to one or more activity criteria to associate each neural activity profile with an associated activity type chosen from a respiratory activity type, a deglutition activity type, a vibration activity type, a reflux activity type, and any combination thereof. A detailed description of activity criteria in various aspects are described in details herein below.

i. Activity Criteria

The activity criteria describe various characteristics of a neural activity profile that may uniquely associate the neural activity profile with a particular upper airway activity including, but not limited to a respiratory activity, a deglutition activity, a vibration activity, and a reflux activity. The characteristics may include ranges, and/or threshold values of neural activity profile characteristics including, but not limited to a time separation of a neural signal feature such as a peak amplitude, a pattern of neural signals, and a signal conduction speed.

Respiratory Activity Criteria

In an aspect, the respiratory criterion indicating a respiratory activity may include: a time separation between peak neural signal amplitudes ranging from about 1 seconds to about 5 seconds; a periodically repeating pattern of neural signals with a period ranging from about 12 patterns per minute to about 60 patterns per minute; and any combination thereof.

Deglutition Activity Criteria

In an aspect, a deglutition criterion indicating a deglutition activity may include: an anterior to posterior neural activation pattern; a stereotyped neural activation pattern with a duration of less than about 1 second; and any combination thereof Vibration Activity Criteria In an aspect, a vibration criterion indicating a vibration activity may include a neural signal frequency ranging from about 10 Hz to about 400 Hz; a time separation between peak neural signal amplitudes ranging from about 1 second to about 5 seconds, and any combination thereof.

Reflux Activity Criteria

In an aspect, a reflux criterion indicating a reflux activity may include a signal conduction velocity of less than about 2 m/s.

e. Activity States

In various aspects of the method, the at least one neural activity profiles may be processed to determine an activity state characterizing the associated activity type. The activity state may include a respiratory state, a deglutition state, a vibration state, and a reflux state.

i. Respiratory State

The respiratory state may include respiratory timing, respiratory amplitude, respiratory phase, respiratory location, and any combination thereof. The respiratory phase may include either an inspiratory phase, expiratory phase, or zero flow phase between inspiratory phase, and expiratory phases. The respiratory phase may be defined for example with reference to peak amplitude in the IRA during each breath, as determined based on a calibration of normal respiration of a given subject using, for example, polysomnographic techniques.

ii. Deglutition State

The deglutition state may include solid contact, fluid contact, contact velocity, contact timing, contact amplitude, contact pressure, contact texture, contact temperature, a presence of an unswallowed bolus, and any combination thereof;

iii. Vibration State

The vibration state may include vibration timing, vibration amplitude, vibration phase, vibration location, vibration pattern, and any combination thereof.

iv. Reflux State

The reflux state may include reflux timing, reflux pH, reflux location, and any combination thereof.

f. Condition of Subject

In an aspect, the at least one activity states may be processed to obtain at least one condition of the subject chosen from a respiratory condition, a deglutition condition, a vibration condition, a reflux condition, and any combination thereof.

i. Respiratory Condition

In an aspect, the respiratory condition may include apnea, tachypnea, hyperpnea, hypopnea, polypnea, dyspnea, bradypnea, cough, Cheyne-Stokes respiration, Biot's respiration, ataxic respiration, Kussmaul respiration, wheezing, irregular respiration, respiratory arrest, restrictive respiration, shallow breathing, hypoventilation and any combination thereof.

ii. Deglutition Condition

In an aspect, the deglutition condition may include presence of unswallowed bolus, occurrence of swallow, occurrence of dysphagic swallow, presence of acid reflux, and any combination thereof.

iii. Vibration Condition

In an aspect, the vibration condition may include snoring, stridor, wheezing vocalization, and any combination thereof.

iv. Reflux Condition

In an aspect, the reflux condition may include esophageal reflux, pharyngeal reflux, laryngeal reflux and any combination thereof.

In various aspects of the method, any one or more of the at least one states, the at least one conditions, the at least one disorders, and any combination thereof may be displayed on a patient monitor device, and/or communicated to a treatment system.

g. Disorder Prediction

In various aspect, the at least one condition may be assessed to predict a disorder chosen from obstructive apnea, central apnea, dysphagia, heart failure, uremia, asthma, cardiac arrest, organ failure, metabolic acidosis, COPD, pulmonary embolism, Ondine's curse, obesity hypoventilation syndrome, laryngeal penetration, aspiration, esophageal reflux, laryngeal reflux, presence of unswallowed bolus in esophagus, acid reflux, GERD, laryngeal penetration, aspiration, aspiration pneumonia, SIDS, Charcot-Marie-Tooth disease and any combination thereof.

In other aspects, the detection and classification of apnea events as described herein is consistent with the detection and classification of apnea events as described in U.S. Patent Application Publication No. 2010/0125310, i.e. involves calculating an index of respiratory activity (IRA) that is indicative of the amplitude and timing of respiratory activity based on the amplitude and timing of a respiratory signal, such as an electroneurogram (ENG) signal from a nerve such as the internal branch of the superior laryngeal nerve (iSLN), or another sensor of respiratory activity as described elsewhere herein. Details for calculating an IRA that is indicative of the amplitude and timing of a respiratory signal are described in U.S. Patent Application Publication No. 2010/0125310, which is incorporated by reference herein in its entirety.

The algorithm executed by the apnea monitoring and detection module implements steps in the processes as discussed in further detail herein below. Upon the detection of an apnea event, the apnea monitoring and detection module sends a trigger to the therapy control module along with an identification of the type of apnea event, i.e. obstructive, central, or mixed; and apnea or hypopnea, depending on the implemented algorithm, which generates a stimulus appropriate for the type of apnea event. Optionally, the apnea monitoring and detection module may also send an indication of the severity level of the apnea event, as well as timing information of previous or continuing respiration patterns, to the therapy control module 1106.

As described in detail in U.S. Patent Application Publication No. 2010/0125310, the outset of an OSA event or a CSA event may be identified by features of the IRA, for example with reference to an upper and a lower threshold as described above. For example, the first instance of a crossing of the upper threshold by inspiration related peaks of the IRA can be used as a criterion for identifying the outset of an OSA event. Alternatively, the peak durations of the RBI ENG may be used to identify the outset of an OSA event by setting an appropriate threshold. For a CSA event, the outset of the CSA event can be identified, for example, by noting the first absence of crossing of the lower threshold by inspiration related peaks, in a set time period. This period of time may be set, for example, to represent the average time between one or more respiration cycles. It should be understood that for both OSA and CSA events, other IRAs may be calculated in order to identify the outset of such an event. For example, peak durations and interpeak intervals of the RBI ENG can be used, by setting appropriate levels and thresholds. It is to be understood that the absence of measurements at a specified level may indicate a CSA event.

Additionally, apnea event severity can be determined from the IRA. For example, severity of the apnea event may be determined by comparing the amplitude of the apneic IRA to that observed during normal breathing. More severe apnea is characterized by IRA peaks having amplitudes far from the upper and lower thresholds, while less severe apnea or hypopnea is characterized by IRA peaks having amplitudes just above or below the upper and lower thresholds. The level of apnea thus determined can be used to adjust the parameters and characteristics of the applied neurostimulation treatment. This may include changing the stimulation waveform, increasing or decreasing the stimulus amplitude, increasing or decreasing the number of stimuli delivered, selecting electrodes in specific locations or changing the number of stimulation electrodes used. Severity levels may be assigned predetermined thresholds. It is to be understood that the number of OSA and CSA severity levels may vary depending on the precision of the circuitry and/or algorithm used.

Apneic events may be further identified as hypopnea events, i.e. OSA events can be distinguished from obstructive sleep hypopnea (OSH) events, and CSA events can be distinguished from central sleep hypopnea (CSH) events with reference to the IRA. For example, an IRA value between a first upper threshold and a second upper threshold, wherein the second upper threshold is higher than the first upper threshold, may be associated with OSH, while an IRA value greater than the second upper threshold, may be associated with OSA. Accordingly, IRA peaks between the two upper thresholds can be identified as OSH while IRA peaks above the second, higher upper threshold can be identified as OSA. Conversely, an IRA value between a first lower threshold and a second lower threshold, wherein the second lower threshold is lower than the first lower threshold, may be associated with CSH, while an IRA value lower than the second lower threshold may be associated with OSA. The range of values for which IRA peaks are defined as OSH as opposed to OSA, as well as CSH as opposed to CSA, may be determined using a calibration process during abnormal respiration of a given subject using, for example, polysomnographic techniques.

It is to be understood that OSH, OSA, CSH and CSA may be subdivided into multiple severity levels depending on the precision of the circuitry and/or algorithm used.

As described above for the OSA and CSA event detection, the variation in IRAs calculated using algorithms other than RBI ENG may also be used to determine the severity of the apneic or hypopneic event.

Apneic events may be further identified by the location(s) of the airway obstruction using, for example, the temporal profile of the IRA activity pattern acquired from a single electrode or sensor. Alternatively, or in addition, an apneic event may be further identified by the location(s) of the airway obstruction using, for example, the temporal pattern of IRA activity acquired across multiple electrodes or sensors, indicating, for example, the instantaneous pressure at multiple locations in the upper airway.

g. Other Uses of Monitoring Methods

Figures 13, 14:
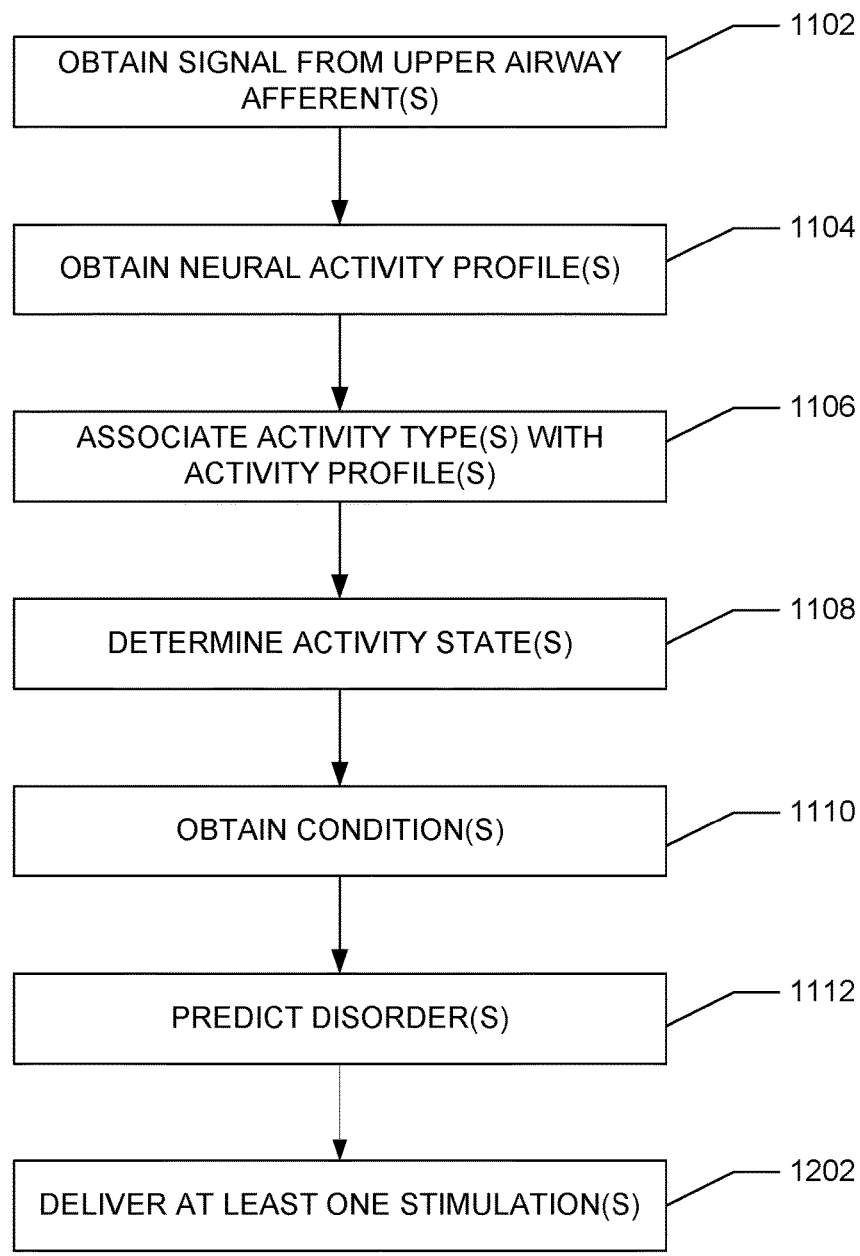
FIG. 13 is a schematic diagram of a method for preventing and/or treating an upper airway condition.
FIG. 14 is schematic diagram of a combined method for monitoring, preventing, and/or treating an upper airway condition.

In various aspects, the upper airway states, conditions, and/or disorders obtained using the method may be displayed or used to drive an alarm or alert. In various other aspects, the upper airway states, conditions, and/or disorders obtained using the method may be used in the implementation of condition prevention/treatment methods as described herein below, or may be transmitted to other devices including but not limited to monitor devices and/or treatment devices. For example, the method in various aspects may detect respiration rate, phase, and timing. This capability provides for general monitoring of vital signs, aside from apnea detection, and may be used to provide respiration-related or other upper airway-related parameters to other devices such as external monitoring equipment, or implanted devices such as pacemakers or implantable defibrillators. The upper airway states, conditions, and/or disorders obtained using the method may be transferred for use to any known implantable apnea treatment devices that terminate apnea using drug delivery, atrial overdrive pacing or electrical stimulation of the nerves or muscles that control respiratory activities 2. Method of Treating and/or Preventing an Upper Airway Disorder FIG. 13 is a flow chart illustrating a method 1200 of preventing and/or treating an upper airway disorder. The method 1200 includes delivering at least one stimulation to a modulate a reflex including, but not limited to a swallowing reflex and/or a negative-pressure reflex.

a. Disorders

In an aspect, the method 1200 prevents and/or treats an upper airway disorder including, but not limited to: obstructive apnea, central apnea, obesity hypoventilation syndrome, dysphagia, esophageal reflux, presence of unswallowed bolus in esophagus, acid reflux, GERD, and any combination thereof;

b. Stimulation of Reflex i. Reflexes Overview

In an aspect, the method 1200 delivers at least one stimulation to a modulate a reflex including, but not limited to a swallowing reflex and/or a negative-pressure reflex.

ii. Swallowing Reflex

As used herein, the term "swallow" refers to all or part of swallow sequence. Swallow stimuli are at least one of: electrical stimulation to at least one swallow-related nerve, electrical stimulation to at least one swallow-related muscle, and mechanical stimulation to at least one swallow-related sensory receptor.

Without being limited to any particular theory, the act of swallowing activates and repositions airway structures that are commonly involved in obstructive sleep apnea. In various aspects, stimulation of the swallow reflex may be used effectively to reposition airway structures, between breaths, to reestablish airway patency. Specifically pharyngeal reflexes are exploited to treat upper airway disorders. A swallow activates all of the structures that are commonly involved in OSA including the tongue, soft palate, epiglottis, and pharyngeal walls. In addition, the swallow includes active components at the end of the sequence that return pharyngeal structures to their "normal" positions. Triggering the swallow reflex in OSA subjects may activate and reposition any dysfunctioning pharyngeal structures and return the airway to a patent state.

In various aspects, a swallow stimulus may include an electrical or mechanical stimulus to a reflex-related nerve, muscle, or sensory receptor in the subject that is sufficient to elicit all or part of the reflexive and pre-programmed coordinated activity of a swallow. For example, the swallow stimulus may include electrical stimulation to at least one swallow-related nerve, electrical stimulation to at least one swallow-related muscle, mechanical stimulation to at least one swallow-related sensory receptor in the skin or mucosa of the subject, or any combination thereof provided that the swallow stimulus is sufficient to elicit all or part of a swallow sequence in the subject. Stimulation of multiple targets may be delivered simultaneously, or in a sequence designed to elicit natural activation patterns in all or part of the 50 muscles normally involved in the swallow sequence. For electrical stimuli, the stimulus target may be an afferent nerve or an efferent nerve, and may include at least two swallow-related nerves wherein each swallow-related nerve is independently an afferent nerve or an efferent nerve. An afferent target is selected based on the ability of the afferent nerve, when stimulated, to elicit all or part of reflexive swallow pattern activity from the central nervous system of the subject. The target nerve may be, for example, the internal branch of the superior laryngeal nerve (iSLN), or the pharyngeal branch of the glossopharyngeal nerve. Alternatively or in addition, the swallow-related nerve may be an efferent nerve. An efferent target is selected based on the ability of the efferent nerve, when stimulated, to elicit motor activity in at least one effector in a swallow sequence, the motor activity comprising all or part of a swallow sequence in the subject. Mechanical stimulation may comprise stimulation to at least one swallow-related sensory receptor in the skin or mucosa of the subject, such as for example delivery of a liquid to at least one of the oral, nasal, or pharyngeal cavity of the subject that is sufficient to elicit all or part of a swallow sequence in a subject.

Treatment of Apnea Using Swallowing Reflex Stimulation

In an aspect, the method 1200 may be used to reposition and hold the pharynx in a patent state by triggering a swallowing reflex in order to treat apnea. Any system and method described herein which involves detection of a swallow may be used to deliver a swallow stimulus during or concurrent with detection of a swallow, for example to augment a spontaneously occurring swallow. Any system and method described herein which involves detection of a dysphagic swallow, may be used to deliver a swallow stimulus during or concurrent with detection of the dysphagic swallow, for example to assist with initiation of a non-dysphagic swallow.

Treatment of Dysphagia Using Swallowing Reflex Stimulation

In an aspect, dysphagia may be treated by delivering a swallow stimulus. For example, the methods and systems may be suitably configured to deliver preventative mechanical or electrical stimulation of swallow in order to prevent dysphagia before dysphagia occurs using an open loop system that is not configured to rely on a dysphagia or swallow detection event. The methods and systems may also be suitably configured to deliver preventative mechanical or electrical stimulation of swallow in order to prevent dysphagia using a closed loop system that is configured to detect a bolus or attempted swallow in a dysphagic patient. In another aspect, the method may also used to deliver therapeutic mechanical or electrical stimulation of a swallow in order to treat dysphagia during a dysphagic swallow using a closed loop system that is configured to detect a dysphagic swallow in a dysphagic patient.

The stimulated swallow may propel the bolus, clear the airway and prevent penetration or aspiration of saliva, mucus, and/or a bolus of fluid. In an additional aspect, the method may also be used to train, strengthen and coordinate spontaneous (i.e. unstimulated) patient-initiated swallows. In another additional aspect, the swallow stimulus may be triggered by means of a manual input by the subject; for example, the subject may trigger a swallow stimulus to enhance a dysphagic swallow.

Treatment of GERD Using Swallowing Reflex Stimulation

In an aspect, the method may be used to treat GERD using stimulation of the swallow reflex. Esophageal exposure to gastric juice is normally minimized chemically by saliva and mechanically by esophageal peristalsis. In GERD patients, esophageal motility, particularly secondary peristalsis, is impaired and results in increased duration of exposure to acid. "Also, sleeping people tend to swallow less frequently. This slows the regular esophageal contractions that normally keep food moving down the esophagus and prevent acid from moving back up. Sleepers also produce less saliva, which plays a role in returning esophageal pH levels to normal after an incident of acid reflux." The present invention describes neurostimulation of pharyngeal afferents to decrease both esophageal and extraesophageal symptoms of acid reflux, by inducing swallow and thus induce primary esophageal peristalsis, clear the upper digestive tract, and return acidic gastric juices to the stomach.

iii. Negative-Pressure Reflex

A negative pressure stimulus is at least one of: electrical stimulation to at least one negative pressure reflex-related nerve, electrical stimulation to at least one negative pressure reflex related muscle, and mechanical stimulation to at least one negative pressure reflex-related sensory receptor. Any of these stimuli may be delivered as one or more (as series of) discrete stimulus bursts designed to elicit at least one negative pressure reflex per each burst. Mechanical stimulation for eliciting the negative pressure reflex includes, in non limiting example, a pulling vacuum. Electrical nerve stimulation for eliciting the negative pressure reflex may include, in non limiting example, stimulating the iSLN. Electrical muscle stimulation for eliciting the negative pressure reflex includes but is not limited to electrical stimulation of the tensor palatini, hypoglossal, and/or superior pharyngeal constrictor. Efferent nerve stimulation for stimulating the negative pressure reflex includes the nerves innervating the tensor palatini, genioglossus, and/or pharyngeal constrictor muscles.

In any method or system using stimulation of the negative pressure reflex, signals from the iSLN may be monitored and the monitored signals may be used to trigger negative pressure reflex stimulation and thereby trigger the reflex, and/or to synchronize delivery of the stimulation to occur during a certain phase of the respiratory cycle.

In any of the above systems including fully open, partially open, partially closed and fully closed, monitoring of iSLN signals can be used for synchronization and/or triggering of the negative pressure reflex stimulus. Further, signals from sensors, or from nerves other than iSLN may be monitored for synchronization and/or triggering of the stimulus, as described herein above with respect to delivery of a negative pressure reflex stimulus.

Treatment of Apnea Using Negative Pressure Reflex Stimulation

In another aspect, negative pressure reflex stimulation may be used for as a therapy for apnea, wherein negative pressure reflex stimulation is any stimulation sufficient to elicit all or part of the negative pressure reflex, which stiffens, repositions and/or holds the pharynx in a patent state. Thus, negative pressure reflex stimulation serves to stiffen, reposition and/or hold the pharynx in a patent state.

ii. Stimulation of Reflexes

In other aspects, the swallow reflex and/or negative pressure reflex may be stimulated by delivering an electrical stimulation and/or a mechanical stimulation, defined herein below.

iii. Type of Stimulation

A burst of electrical or mechanical stimulation is defined here as a temporally discrete occurrence of one (a single), or more (a series) of stimulus pulse(s), defined by a total duration from burst start to burst end of about 200 μsec to about 3 seconds.

Nerve stimulation means may be accomplished by any means including, but not limited to direct, transcutaneous, magnetic, electrical, optical, mechanical or any other means. Receptor stimulation may be accomplished by any means including, but not limited to, direct, transcutaneous, magnetic, electrical, optical, mechanical or any other means. Access to the nerve or receptor by any means, electrode and lead, injectable bion-like platform, light through skin, magnetic stimulation through skin, electrical stimulation through skin, communication transcutaneously, percutaneously, a fully implanted, partially implanted, or fully external system. Biological, mechanical or electrical sensors may be used to provide information for the configuration of the stimulation.

Electrical Stimulation

In various aspects, each electrical stimulation may be delivered to a reflex-related nerve, a reflex-related muscle, a reflex-related sensory receptor, and any combination thereof. The reflex-related nerve comprises: an afferent chosen from iSLN branch of vagus nerve, pharyngeal branch of vagus nerve, pharyngeal branch of glossopharyngeal nerve, tonsilar branch of glossopharyngeal nerve, lingual branch of glossopharyngeal nerve, intermediate nerve, palantine nerve, greater petrosal nerve, any branch of facial nerve, and pterygopalatine nerve of trigeminal nerve; or an efferent chosen from: recurrent laryngeal nerve, external branch of superior laryngeal nerve, brancial motor branch of glossopharyngeal nerve and proximal fibers, mandibular nerve, medial pterygoid nerve, pharyngeal branch of vagus nerve and proximal fibers; branch of facial nerve and proximal fibers, and branch of hypoglossal nerve and proximal fibers.

The stimulus target may be an afferent nerve or an efferent nerve, and may include at least two swallow-related nerves wherein each swallow-related nerve is independently an afferent nerve or an efferent nerve. An afferent target is selected based on the ability of the afferent nerve, when stimulated, to elicit all or part of reflexive swallow pattern activity from the central nervous system of the subject. The target nerve can be, for example, the internal branch of the superior laryngeal nerve (iSLN), or the pharyngeal branch of the glossopharyngeal nerve. Alternatively or in addition, the swallow-related nerve can be an efferent nerve. An efferent target is selected based on the ability of the efferent nerve, when stimulated, to elicit motor activity in at least one effector in a swallow sequence, the motor activity comprising all or part of a swallow sequence in the subject. The target nerve can be, for example, the recurrent laryngeal nerve, the external branch of the superior laryngeal nerve, the brancial motor branch of the glossopharyngeal nerve, the mandibular nerve, the medial pterygoid nerve, or pharyngeal branch of the vagus nerve.

An electrical swallow stimulus may comprise electrical stimulation to at least one swallow-related nerve or at least one swallow-related muscle, provided that the stimulation is sufficient to elicit all or part of a swallow sequence in the subject.

A swallow stimulus may therefore, alternatively or in addition to, comprise mechanical stimulation to at least one swallow-related sensory receptor, such as a mechanoreceptor, in the skin or mucosa of the subject.

Mechanical Stimulation

In an aspect, each mechanical stimulation may be delivered to a reflex-related sensory receptor. The reflex-related sensory receptor may be situated in the skin or mucosa of the subject. Non-limiting examples of reflex-related sensory receptors include: a mechanoreceptor sensitive to negative airway pressure, positive airway pressure, stretch, position, shear, slip, vibration, texture, touch, mechanical compression, muscle stretch, muscle drive, air flow, blood pressure or blood osmolarity; a chemoreceptor sensitive to $CO_2$, $O_2$, or pH; a thermoreceptor sensitive to temperature or airflow; and a nociceptor sensitive to polymodal pain. Swallow stimuli may include temporally discrete stimulus bursts configured to elicit at least one swallow per each burst, but also a continuous stimulus delivery, such as but not limited to delivery to the oral cavity of a continuous "dribble" of fluid such as water or juice. A "dribble" is a continuous but slow rate of fluid flow, as determined by one of average skill, but in non-limiting example is about 1 ml/minute or within the range of 0.5 ml/minute to about 5 ml/minute.

iv. Stimulation Devices

In any of the systems described herein, the stimulation output device is configured to generate one or more stimuli that target at least one swallow-related nerve or muscle, or swallow-related receptor, to elicit all or part of the reflexive and pre-programmed coordinated activity of a swallow.

Electrical Stimulation Devices

A stimulation electrode may be placed in, around or near a peripheral nerve that carries afferent and/or efferent neural activity. Depending on the choice of stimulation output device, an alternative system may include a therapy output device including an electrical stimulation output device.

Any system may be further configured to control, or to control and deliver a swallow stimulus to multiple targets. Selection of targets for stimulation may vary depending on the identified apneic event and the type (mechanical, electrical or combination thereof) of stimulation used. The system may be configured for example with a single electrode that is used as both a recording and stimulation electrode, for example when the iSLN is used for both recording and stimulation. Furthermore, multiple electrodes may be used, some or all of them being used both as recording and stimulation electrodes while others are used only as recording or stimulation electrodes.

The electrodes may be, for example, cuff electrodes such as, but limited to, that described in U.S. Pat. No. 5,824,027. Other types of electrodes, leads, probes, cuff-electrodes, etc., may be used as well. Other examples of cuff electrodes that may be used are disclosed in U.S. Patent Application Publication No. 2008/0065184 entitled "NERVE CUFF, METHOD AND APPARATUS FOR MANUFACTURING SAME", published Mar. 13, 2008, by Hoffer et al. and PCT Patent Application Publication No. WO 2008/025155 entitled "NERVE CUFF INJECTION MOLD AND METHOD OF MAKING A NERVE CUFF", filed Aug. 29, 2007, by Imbeau et al. both of which are hereby incorporated by reference in their entirety.

Mechanical Stimulation Devices

A mechanical stimulation device may be used for oral, nasal or pharyngeal delivery of a mechanical stimulus to the subject. The mechanical stimulation entails delivery of an amount of a liquid of relatively low viscosity such as water or saline, to the oral, nasal, or pharyngeal cavity of the subject. The amount of liquid may be delivered as a continuous flow, or may delivered as a small discrete bolus, for example about 0.1 ml up to about 10 ml, preferably about 0.5 ml to about 2 ml, delivered as short a burst with an overall duration between about 200 μsec to about 3 seconds. For example, the mechanical stimulus may comprise a continuous delivery of a liquid at a flow rate of about 1 ml/minute over the course of the entire night. Alternatively, the liquid may be delivered as discrete bursts of liquid, as described further below.

In an aspect, a liquid delivery device may be operatively coupled to the stimulation module via a wire lead or wireless communication (not shown), and the stimulation module may be configured to generate the mechanical swallow stimulus through the liquid delivery device. In various aspects, the liquid delivery device may include a gravity-fed spout or a tube coupled to a liquid reservoir via a solenoid valve configured to open and close in response to electrical signals from the stimulation module. It should be understood that any device or apparatus can be used for liquid delivery device, provided that it is capable of containing or providing a volume of liquid of at least about 0.5 ml, and includes an element such as the solenoid valve that can control the timing and volume of liquid delivery.

iv. Subthreshold Versus Suprathreshold Reflex Stimulation

In various aspects, each of the at least one stimulations may be delivered at subthreshold parameters insufficient to independently elicit the reflex or at suprathreshold parameters sufficient to independently elicit the reflex. The method in an aspect may be used to provide sensory enhancement to augment the detection of weak sensory signals by adding noise to the signal that is configured to improve the ability of spontaneously occurring sensory signals to trigger neural responses. Such systems and methods use stimulation configured using the principles of stochastic resonance phenomena, wherein the stimulation is can provide afferent facilitative stimulation to the iSLN to improve negative pressure reflex for apnea patients.

Each of the at least one stimulations may include: a subthreshold electrical stimulation delivered to the reflex-related nerve or to the reflex-related sensory receptor to reduce the threshold of the reflex, to maintain muscle tone, and any combination thereof; a subthreshold electrical stimulation delivered to the reflex-related muscle to maintain muscle tone; a subthreshold mechanical stimulation delivered to the reflex-related sensory receptor to reduce the threshold of the at least one reflex; a suprathreshold electrical stimulation delivered to the reflex-related nerve, the reflex-related sensory receptor, the reflex-related muscle, or any combination thereof to maintain muscle tone, position and/or posture of one or more respiratory and/or deglutition structures of the subject; a suprathreshold mechanical stimulation delivered to the reflex-related sensory receptor to maintain muscle tone, position and/or posture of one or more respiratory and/or deglutition structures of the subject; a suprathreshold electrical stimulation delivered to the reflex-related nerve, the reflex-related sensory receptor, the reflex-related muscle, or any combination thereof to treat the disorder; and a suprathreshold mechanical stimulation delivered to the reflex-related sensory receptor to treat the disorder.

Subthreshold Electrical Stimulation Characteristics

In an aspect, the method may augment neural signal initiating, and/or control negative pressure reflex in apnea patients using a "background pulse train" delivered to iSLN. The firing rate of the background pulse train is intentionally subthreshold and so as not to trigger the reflex independently. Rather, the background pulse train merely augments the weak firing rate resulting from naturally occurring sensory stimuli such as the negative pressure signal on iSLN during sleep in apneic patients. The additive effect of the weak firing rate due to the naturally occurring stimuli, with the added background pulse train, results in a suprathreshold firing rate which elicits the desired response, for example the negative pressure reflex. The background pulse train may be individual pulses or bursts of pulses. An interpulse interval, which refers to the time between the end of one delivered pulse and the beginning of the next pulse, may be approximated by white noise or noise filtered using one or more of a band pass, high pass or low pass filter. Such stimuli may be delivered with or without regard to respiratory phase or apnea event, or may be adjusted to occur during desirable phases of respiratory cycle or during period when apnea is likely to occur.

The timing and frequency of a background pulse train may be varied. A background pulse train can be composed for example of single pulses delivered with an interpulse interval approximated by a band pass noise centered around, e.g. about 1 second. A background pulse train could be composed for example of bursts of pulses, each burst lasting tens of seconds (e.g. 10 sec, 20, 30 sec or more), which are delivered at an interburst interval approximated by a band pass noise centered around a predetermined time period of one or more minutes (e.g. 1-10 minutes, for example 5 minutes), or of single pulses delivered at intervals centered around 1 minute, or single pulses delivered at intervals centered around ~30 seconds, or single pulses delivered at intervals centered around ~30 seconds stimuli adjusted to occur during desirable phase of respiratory cycle.

In an aspect, the method described herein may provide a background pulse train as described herein above to be delivered to the iSLN, to augment neural signal initiating or to control swallow in dysphagia patients using "background pulse train" delivered to iSLN. As described herein above, the firing rate of the background pulse train is purposefully subthreshold and not designed to trigger the reflex independently. The background pulse train may be delivered with or without regard to respiratory phase or presence of a bolus event, or may be adjusted to occur during desirable phases of respiratory cycle and/or during meals. Such stimuli may be delivered with or without regard to respiratory phase or apnea event. Or may be adjusted to occur during desirable phases of respiratory cycle or during period when apnea is likely to occur.

In an aspect, the method described herein can be configured to provide stimulation that augments neural signal initiating or controlling muscle tone (e.g. stretch reflex) in the UAW of apnea or dysphagia patients using "background pulse train" delivered to UAW afferents. As described herein above, the firing rate of the background pulse train is purposefully subthreshold and not configured to trigger movement of the UAW muscles independently. Rather, the background pulse train is configured to augment the weak firing rate of naturally occurring sensory stimuli (e.g. the stretch of UAW muscle spindle afferents via Ia afferent fibers), wherein the additive effects of the weak firing rate due to naturally occurring sensory stimuli together with the background pulse train result in a suprathreshold firing rate which elicits the desired response (e.g. stretch reflex and restoration of UAW muscle tone). The background pulse train may be provided in individual pulses or bursts of pulses. The interpulse interval of the background pulse train may be approximated by white noise or noise filtered using one or more of a band pass, high pass or low pass filter. In such systems and methods, the background pulse train may be delivered with or without regard to respiratory phase or apnea or dysphagia event. Stimulation may comprise selective stimulation of Ia afferents or may include other afferent or efferent fibers. It will be appreciated that increased UAW muscle tone acts to prevent collapse of the UAW. Increased muscle tone also acts to enhance the physiological response to naturally occurring muscle control signals from efferent fibers. Nerves that innervate the UAW muscles include branches of the Facial, Hypoglossal, Vagus and Glossopharyngeal nerves and their proximal fibers. The stimulation may be delivered with or without regard to respiratory phase or apnea or presence of unswallowed bolus or dysphagia event, or may be adjusted to occur during desirable phases of respiratory cycle and/or during meals for dysphagia or during sleep for apnea or snoring.

In an aspect, the method described herein can be further configured to provide stimulation of UAW muscles by continuous direct stimulation of UAW efferents, thereby improving muscle tone for treating apnea or dysphagia. In such systems and methods, stimuli are configured to remain subthreshold and are not capable of eliciting discrete movements but rather only a continuous change in muscle tone. The resulting increase in muscle tone also enhances the physiological response to any naturally occurring efferent control signal(s), and also prevents UAW collapse.

Systems and methods described herein can be further configured to stimulate co-contraction for UAW muscle tone by continuous direct stimulation of UAW efferents to opposing muscle groups, to elicit co-contraction of muscles. Such stimulation may be used to treat apnea or dysphagia. Such stimuli remain subthreshold and are not capable of eliciting discrete movements but rather only a continuous change in muscle tone.

Suprathreshold Electrical Stimulation Characteristics

In various aspects, the method may deliver a burst of stimulation to a reflex-related nerve or muscle, wherein the stimulation may be electrical or mechanical. A burst of stimulation is understood to be one (a single) pulse, or multiple stimulus pulses, wherein the single or multiple pulses together have a minimum duration of about 100-200 μsec, and a maximum duration of about 3 seconds, or about the maximum duration of an inter-breath interval. Amplitude of any stimulus pulse may vary depending on the type of stimulus being used and sensitivity of the individual subject as previously determined. For example, a burst comprising a single pulse of electrical stimulation may have a total duration of about 100-200 μsec. A burst comprising multiple electrical pulses may have a total duration of about 500 μsec to about 3 seconds. A burst comprising multiple electrical pulses may include 3, 5, 10, 20, 30, 40, 50, 60, 70, 80, 90, 100 or more individual electrical pulses.

For electrical stimulation, individual stimulus pulses can have for example an amplitude of at least about 0.1 mA, and a duration of about 100 μsec to about 500 μsec, preferably about 200 μsec, presented as a single pulse, or multiple pulses. Two or more individual pulses can be presented, for example, at a frequency of at least about 20 Hz to about 40 Hz, preferably at about 30 Hz.

The produced stimulation signals may be square pulses or arbitrary waveforms, constant voltage, constant current, single stimuli or bursts of signal pulses. Stimulation location, amplitude, and/or waveform may be adjusted in a closed-loop based on current respiratory conditions such as respiratory phase, or based on conditions relayed by the apnea monitoring and detection module 1104 in response to previous stimulation. Stimulation waveforms may also contain features allowing for selective stimulation using current steering, directionally selective stimulation of efferent or afferent fibers, selectivity for stimulating axons of a particular diameter, or features designed to block transmission of undesired bioelectric activity.

The therapy control module can be configured to generate a signal to the stimulation module to deliver a burst of electrical stimulation to a swallow-related nerve or muscle, wherein a burst is understood to be any series of stimulus pulses delivered at a frequency of between about 20 Hz to about 40 Hz, with a pulse amplitude of greater than about 0.1 mA, a pulse duration of about 200 μsec, and a total burst duration of between about 200 μsec to about 3 seconds; or to deliver a burst of mechanical or electrical stimulation to a swallow-related mechanoreceptor in the skin or mucosa of the subject, wherein a burst is understood to be any series of one or more mechanical stimuli with a total burst duration of between about 200 μsec to about 3 seconds.

Suprathreshold Mechanical Stimulation Characteristics

In an aspect, the method may deliver a burst of mechanical stimulation to a mechanoreceptor in the skin or mucosa of the subject, and may include a single pulse, or multiple stimulus pulses. It will be understood that the minimum achievable duration of each single mechanical pulse will be longer than the minimum achievable duration of each single electrical pulse due to physical limitations inherent in actuating mechanical stimulus delivery. An exemplary burst of mechanical stimulation is one comprised of a single stimulus pulse lasting about 0.5 seconds, the burst having a total duration of about 0.5 seconds. A burst comprised of multiple mechanical stimuli may have a total duration of between about 0.5 and 3 seconds, or up to about the maximum the duration of an inter-breath interval in the subject.

For mechanical stimulation, a burst can comprise a series of one (a single) or more (a series) of mechanical stimulus pulses with a total duration from burst start to burst end of about 200 μsec to about 3 seconds. For mechanical stimulation, two or more individual stimulus pulses may be presented at a frequency of at least about 0.1 Hz to about 10 Hz, preferably about 0.33 Hz. It should be understood however that mechanical stimulation at a frequency approaching the physical limits of the physical apparatus may be faster than 10 Hz and can be used, particularly when pulses of small amplitude are being used. For mechanical stimulation, the characteristics of an individual stimulus pulse are determined by the nature of the mechanical stimulus being used. For example, a fluid mechanical stimulus pulse delivered to a mechanoreceptor in the skin or mucosa of the subject, would have a total volume determined by the flow rate multiplied by the duration of the stimulus pulse. In the case of fluid delivery, a fluid pulse may have a volume of about 0.5 ml to about 5 ml.

The mechanical stimulation may include delivery of an amount of a liquid of relatively low viscosity such as water or saline, to the oral, nasal, or pharyngeal cavity of the subject. The amount of liquid may be delivered as a continuous flow, or may delivered as a small discrete bolus, for example about 0.1 ml up to about 10 ml, preferably about 0.5 ml to about 2 ml, delivered as short a burst with an overall duration between about 200 μsec to about 3 seconds. For example, the mechanical stimulus may comprise a continuous delivery of a liquid at a flow rate of about 1 ml/minute over the course of the entire night. Alternatively, the liquid may be delivered as discrete bursts of liquid, as described further below.

The liquid delivery device may be operatively coupled to a controller via a lead wire or wireless communication link (not shown. The liquid delivery device 1340 may include a gravity-fed spout or tube coupled to a liquid reservoir via a solenoid valve configured to open and close in response to electrical signals from the stimulation module. It should be understood that any device or apparatus can be used for liquid delivery device, provided that it is capable of containing or providing a volume of liquid of at least about 0.5 ml, and includes an element such as the solenoid valve that can control the timing and volume of liquid delivery to the subject.

v. Timing of Stimulation

A swallow initiated during or prior to expiration is considered the safest respiratory phase for swallowing in adult humans and to minimize the potential for food or fluid entering the airway. Each of the at least one stimulations may be delivered either according to a predetermined schedule (open loop) such as random or periodic, or in response to at least one stimulation signal (Partially open loop and closed loop), and any combination thereof. The at least one stimulation signal may be received from a patient monitor device or using methods described herein above to identify event and generate stimulation signal.

The at least one stimulation signal may be generated when: the disorder is predicted to time the delivery of the at least one stimulation to coincide with an occurrence of the disorder; the respiratory phase is an exhalation phase to time the delivery of the at least one stimulation to coincide with an exhalation of the subject; and any combination thereof.

In various aspects, the methods described herein above may determine an expiration phase and generate a signal to deliver the stimulus burst such that delivery of the stimulus is timed to coincide with the occurrence of expiration or zero flow phase, i.e. between and not during inspiratory phases.

A pulse generator may provide current and/or voltage stimulation signals to muscles, nerves or tissue. Examples of pulse generators that may be used but are not limited to those described in U.S. patent application Ser. No. 11/920,814 entitled "IMPLANTABLE PULSE GENERATOR", filed on Oct. 9, 2007, by Roy et al. which is hereby incorporated by reference in its entirety.

Another exemplary process involves application of bursts of electrical or mechanical stimulation as the swallow stimulus, and further involves a timing requirement such that the delivery of the burst stimulation is timed to coincide with the expiratory phase or zero flow phase of respiration in the subject. The result is that the stimulus burst is delivered between inspiratory phases of the subject. This method is advantageous in constraining elicited swallow to respiratory phases considered safest for swallow in adult human subjects, and also to avoid undesirable side effects of iSLN stimulation, including central apnea.

Open Loop Stimulation

In an aspect, the reflex stimulation may be delivered according to a delivery schedule chosen from periodic, random, and continuous to implement an open loop stimulation. In an aspect, the method may deliver preventative mechanical or electrical stimulation of swallow for prevention of apnea before apnea occurs, or in an open loop system that is not configured to rely on an apnea detection event. The system may be configured, for example, to deliver or mechanical or electrical stimulation capable of eliciting swallow, continuously or at regular or random intervals. The methods and system may thus be configured to reposition and hold the pharynx in a patent (open) state. Such a configuration is thus preventative and delivered without regard to presence or absence of apnea and without regard to respiratory phase. The system may thus be deemed fully open loop.

The methods and systems also encompass those in which detection of apnea is not performed prior to delivery of a therapy such as swallow therapy. In other words, delivery of swallow therapy may be decoupled from apnea detection, such that the swallow therapy is simply delivered continuously, e.g. as a swallow stimulus consisting of continuous fluid flow to the oral cavity, or in periodic bursts of fluid or as periodic burst of electrical stimuli to a nerve or effector muscle. Additionally, swallow therapy that is decoupled as described from apnea detection may be used to treat other indications, such as but not limited to snoring and dysphagia.

Partially Open Loop Stimulation

The methods and system may also use mechanical or electrical stimulation of swallow for apnea, which is capable of eliciting swallow delivered at semi-regular or semi-random intervals. Such a configuration also repositions and holds the pharynx in a patent (open) state. In such a system, stimulation is still preventative and delivered without regard to presence or absence of apnea. The system may be deemed partially open loop, in that stimuli are synchronized to occur during desirable phase of respiratory cycle.

The methods and system may use triggered mechanical or electrical stimulation of swallow for apnea, wherein stimuli that are capable of eliciting swallow is delivered following apnea detection. In such a system, stimulation repositions and hold pharynx in patent state, stimulation may be considered therapeutic because it follows apnea detection, but once stimulation is triggered it is delivered without regard to respiratory phase. The system may be deemed partially closed loop, in that stimuli are triggered by apnea detection but then delivered without regard to respiratory phase.

In normal breathing, expiration commonly occurs at a fixed interval after the offset of iSLN stimulus burst, for example at a threshold of about 2 seconds in an unanesthetized canine, which in part determines breathing rate. Systems and methods as described herein can be configured to promote faster breathing rate by reducing the interval between the offset of the iSLN stimulus burst and the beginning of expiration, thereby increasing blood oxygen level more quickly than otherwise following occurrence of an apneic event. Such an approach may also be used to induce breathing during a central apnea.

Closed Loop Stimulation

Additionally, other inputs obtained by neural monitoring may be used to trigger or synchronize delivery of the swallow therapy.

A fully closed loop system as described in detail herein above includes triggered and synchronized mechanical or electrical stimulation of the swallow, i.e., stimuli capable of eliciting swallow delivered during identified apnea. This system is also configured to reposition and hold the pharynx in a patent state; however the stimulation is therapeutic and also synchronized to occur during a certain phase of the respiratory cycle. The system is thus deemed fully closed loop.

In any of the above systems including fully open, partially open, partially closed and fully closed, monitoring of iSLN signals can be used for synchronization and/or triggering of the stimulus. Further, signals from sensors, or from nerves other than iSLN may be monitored for synchronization and/or triggering of the stimulus. For example, various implantable devices have been described which detect apnea by monitoring the bioelectric activity of the diaphragm, intercostal muscles, or their efferent nerves. Other devices monitor the bioelectric activity of upper airway muscles or their efferent nerves. Still others monitor implanted sensors for indications of, for example, thoracic pressure or blood oxygenation. Any of these and comparable devices can be used for monitoring of signals which are then used to trigger and/or synchronize the stimulus.

2. Combined Method of Monitoring, Treating, and/or Preventing a Disorder

In another aspect, the method may combine monitoring methods and treatment/prevention methods described herein previously. FIG. 14 is a flow chart illustrating the method in an aspect. In this aspect, at least one neural signal is obtained from an upper airway afferent such as an iSLN using a measurement device such as a nerve electrode at step 1102. The at least one neural signal may be amplified and processed using an algorithm such as a rectification and bin-integration (RBI) algorithm to obtain one or more neural activity profiles at step 1104. In this aspect, the one or more neural activity profiles may be compared to one or more activity criteria to associate each neural activity profile with an associated activity type at step 1106. Based on its associated activity type, each neural activity profile is processed at step 1108 to determine one or more activity states characterizing the profile. For example, for a neural activity profile associated with a reflux activity type, one or more reflux states may be obtained at step 1108 including, but not limited to: reflux timing, reflux pH, reflux location, and any combination thereof. In another aspect, the one or more activity states may be processed to obtain at least one condition of the subject at step 1110. In another aspect, the at least one condition may be assessed at step 1112 to predict a disorder. In this other aspect, the disorder may represent a broader characterization of the subject's health or physiological status. For example, if one or more reflux conditions were obtained at step 1110, a related disorder including, but not limited to GERD or acid reflex may be predicted at step 1112. In another aspect, the one or more disorders may be further processed to trigger the delivery of at least one stimulation at step 1202.

III. Systems for Monitoring, Preventing, and/or Treating an Upper Airway Condition/Disorder

1. Overview

Figure 15:
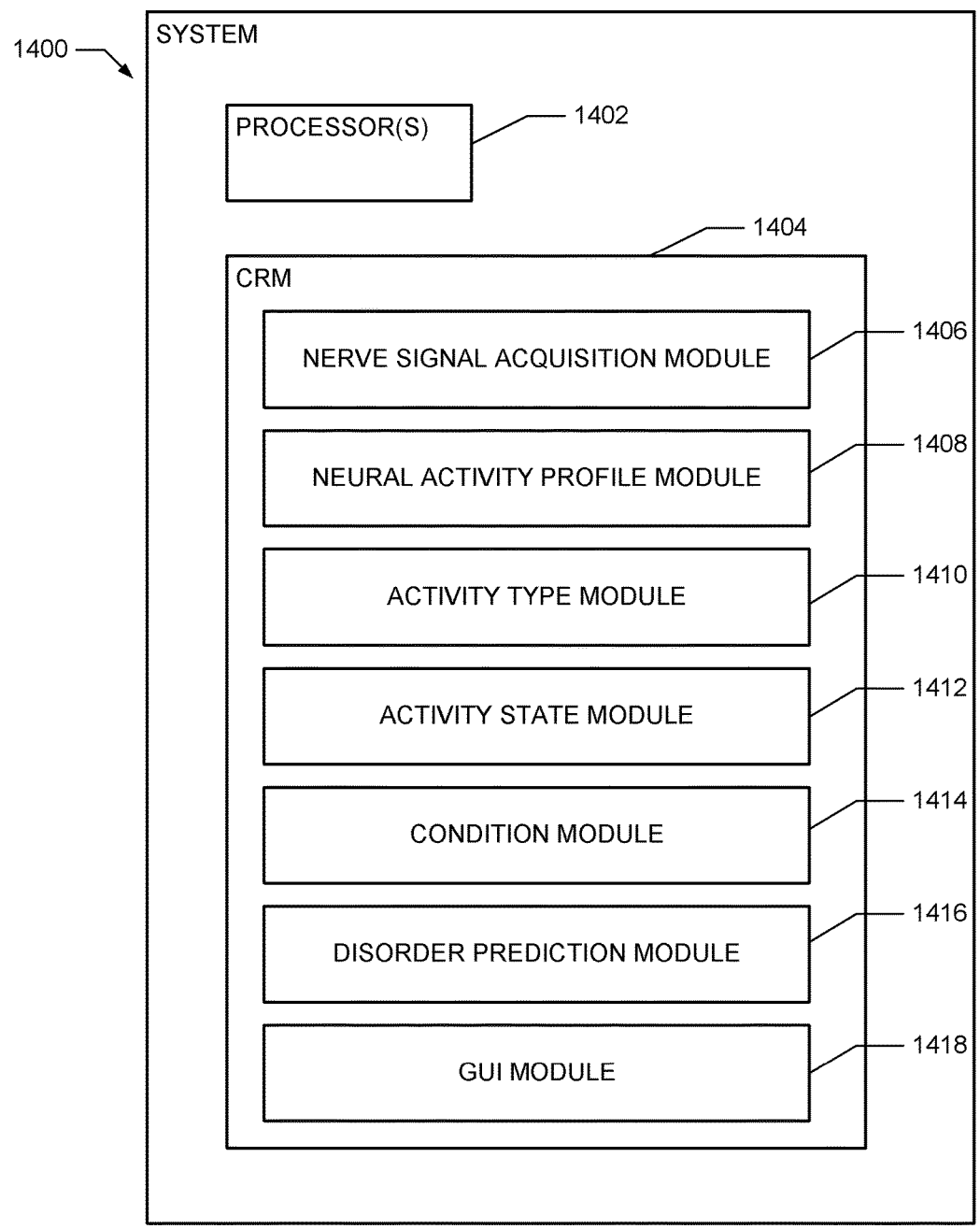
FIG. 15 is a schematic diagram of a system for monitoring an upper airway condition.

A system 1400 for monitoring a upper airway condition is illustrated schematically in FIG. 15. The system 1400 includes one or more processors 1402 and a Cardio Respiratory Monitoring (CRM) 1404 containing a condition monitor application including a plurality of modules.

a. Neural Signal Acquisition Module

In an aspect, a neural signal acquisition module 1406 obtains one or more neural signals in one or more upper airway afferents of the subject.

b. Neural Activity Profile Module

In an aspect, a neural activity profile module 1408 processes each of the one or more neural signals to obtain at least one neural activity profile, each neural activity profile characterized by at least one of: a neural signal timing, a neural signal amplitude, a neural signal phase, a neural signal position, a neural signal conduction velocity, and any combination thereof;

i. Activity Type Module

In an aspect, an activity type module 1410 compares each of the at least one neural activity profiles to one or more activity criteria to associate each neural activity profile with an associated activity type chosen from a respiratory activity type, a deglutition activity type, a vibration activity type, a reflux activity type, and any combination thereof;

ii. Activity State Module

In an aspect, an activity state module 1412 processes each of the at least one neural activity profiles to determine an activity state characterizing the associated activity type. The activity state may include, but is not limited to: a respiratory state comprising respiratory timing, respiratory amplitude, respiratory phase, respiratory location, and any combination thereof; a deglutition state comprising solid contact, fluid contact, contact velocity, contact timing, contact amplitude, contact pressure, contact texture, contact temperature, a presence of a unswallowed bolus, and any combination thereof; a vibration state comprising vibration timing, vibration amplitude, vibration phase, vibration location, vibration pattern, and any combination thereof; and a reflux state comprising reflux timing, reflux pH, reflux location, and any combination thereof; and iii. Condition Module In an aspect, condition module 1408 processes the at least one activity states to obtain at least one condition of the subject chosen from a respiratory condition, a deglutition condition, a vibration condition, a reflux condition, and any combination thereof.

iv. Disorder Prediction Module

In an aspect, a disorder prediction 1416 assesses the at least one condition to predict a disorder chosen from: obstructive apnea, central apnea, dysphagia, heart failure, uremia, asthma, cardiac arrest, organ failure, metabolic acidosis, COPD, pulmonary embolism, Ondine's curse, obesity hypoventilation syndrome, laryngeal penetration, aspiration, esophageal reflux, laryngeal reflux, presence of unswallowed bolus in esophagus, acid reflux, GERD, laryngeal penetration, aspiration, and any combination thereof.

v. GUI Module

In an aspect, a GUI module 1418 generates one or more forms used to receive inputs to the system and to deliver output from the system.

3. Disorder Treatment Application

Figure 16:
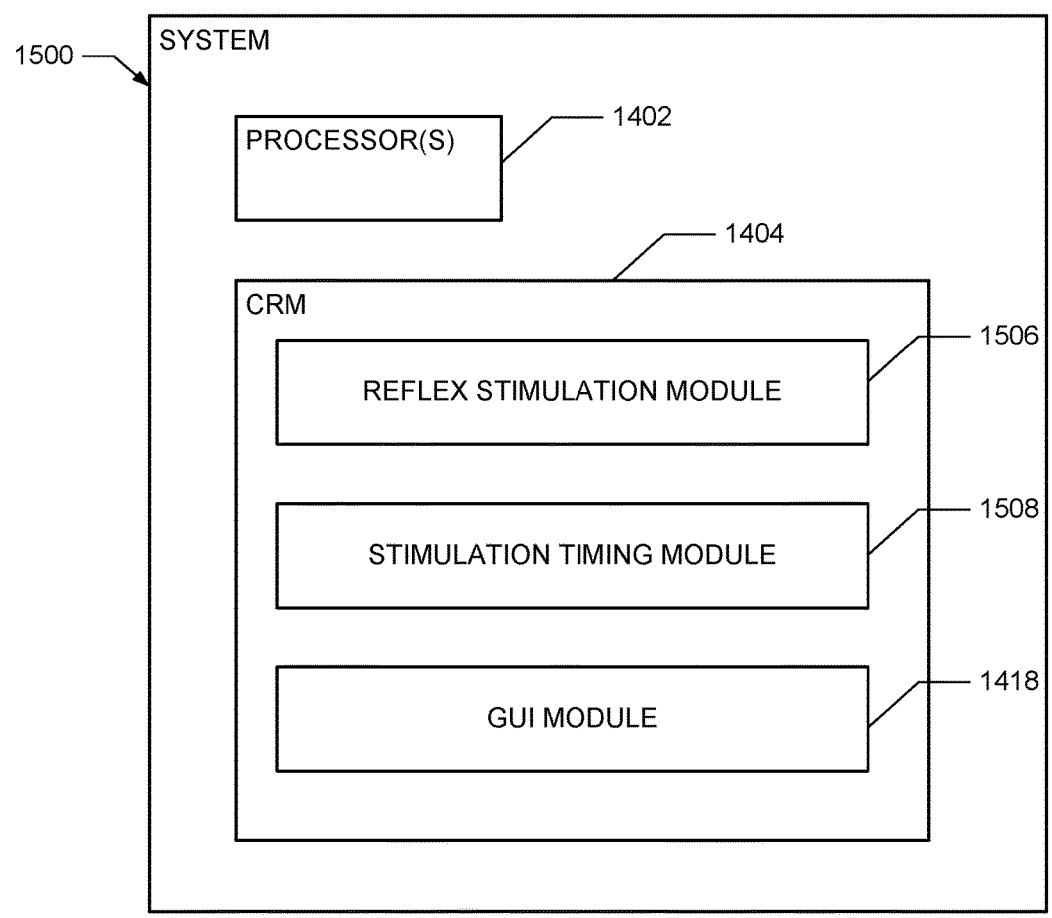
FIG. 16 is a schematic diagram of a system for preventing and/or treating an upper airway condition.

A system 1500 for preventing and/or treating a upper airway condition or disorder condition is illustrated schematically in FIG. 16. The system 1500 includes one or more processors 1402 and a CRM 1404 containing a disorder treatment application including a plurality of modules.

a. Reflex Stimulation Module

In an aspect, a reflex stimulation module 1506 delivers at least one stimulation to modulate at least one reflex chosen from a swallowing reflex, a negative-pressure reflex, and any combination thereof.

b. Stimulation Timing Module

In an aspect, a stimulation timing module 1508 times the delivery of each of the at least one stimulations according to a predetermined schedule or in response to at least one stimulation signal, and any combination thereof. The stimulation timing module 1508 may receive a signal from patient monitor system or from an integrated condition monitor system as described herein previously

4. Combined Monitor/Treatment Application

FIG. 17 is a block diagram of a combined monitoring and prevention/treatment device 1600. The device 1600 combines the modules of the systems 1400 and 150o illustrated in FIGS. 15 and 16 and described herein above.

Having now described the present disclosure in detail, examples will be more clearly understood by reference to the following examples of laboratory test procedures and methods which are included for purposes of illustration only and not intended to limit the scope of the present disclosure.

EXAMPLES

Example 1

Testing of Fluid Stimuli

Subjects are fitted with a nasal catheter and fully instrumented for polysomnography. The nasal catheter is a commercially available, Luer-lock, one-eyed, pediatric feeding tube with an outer 4 French diameter. The catheter is lubricated with a non-analgesic lubricant and advanced transnasally into the pharynx. The fluid delivery port of the catheter is positioned ~2 cm rostral to the upper esophageal sphincter (Dua et al., 2007) and oriented toward the posterior pharyngeal wall. Catheter position is verified laryngoscopically before being fixed in place using tape at the nostrils. A small diameter catheter is chosen to minimize possible increases in airway resistance which may influence swallowing patterns relative to respiration. A small catheter may also eliminate the need for analgesic lubricants, which have been shown to influence swallow function.

The optimal parameters for pharyngeal swallow stimulation in any given subject using fluid delivery are determined. Stimulus flow, volume, and timing are controlled in using a high accuracy peristaltic pump (Harvard Instruments, model 77). The pump is capable of flow rates from 0.01-750 ml/minute and can be controlled remotely using TTL logic. The pump is controlled using control logic from a digital signal processing workstation (Tucker-Davis Technologies RX5). To reduce acoustic and electrical noise, the pump and digital control unit are isolated in an adjacent room and connected to the nasal catheter by a length of tubing.

Inspiration is detected using an abdominal piezoelectric belt and used to control stimulation in real-time. Stimuli can be appropriately timed for delivery between breaths to elicit swallow during the between breath interval while maintaining normal respiratory drive. Stimulation begins shortly after the end of inspiration and is timed (based on respiration rate) to end before the onset of the subsequent inspiration.

Example 2

Determination of Swallow Stimulus Thresholds

Swallow threshold measurements are carried out in awake subjects in the upright position. Subjects are fully instrumented for stimulation and recording, and stimulation is timed to occur in bursts between successive inspirations. All fluid stimuli consist of room-temperature, bottled "Sterile Water for Irrigation, USP" obtained from a medical supplier.

Thresholds are determined at a number of preselected flow rates. For each measurement, a flow rate is fixed and stimulus duration changed between successive stimuli until threshold is determined. The resulting stimulus volumes are calculated as flow X duration. Stimuli are delivered in discrete bursts between successive inspirations. Threshold events are defined as swallow, laryngeal reflex, or subject indication of discomfort. One goal of threshold measurements is to define the shortest duration/smallest volume that will reliably elicit swallow to single stimulus bursts. Another goal is to define stimuli that minimize the potential for discomfort, expulsive reflexes, or sensory arousal during sleep.

A minimum flow rate of 1 ml/minute is used. Additional flow rates are selected at increasing 2× intervals up to the limits of the equipment or subject acceptance. To obtain an upper estimate of acceptable flow rates, informal testing in adult humans has been performed, using water delivered orally through an 8 French catheter. Stimulation at a flow rate of ~5 ml/sec (~300 ml/minute) did not produce discomfort. Subject feedback is collected during the threshold measurement process and stimuli eliciting discomfort (e.g. at high flow rates or volumes) are eliminated from further testing.

Stimulus durations start at a minimum of 0.5 seconds and selected at increasing 0.5 second intervals to a maximum of 3.0 seconds. The maximum 3.0 second duration is estimated from normal waking respiration of 10-12 breaths/minute (5-6 second interval) (Dozier et al, 2006) and assuming a 50% duty cycle for inspiration. Preselected flow rates and durations result in the stimulus volumes shown in the table below. These volumes include the full range of threshold volumes reported for single swallows in previous studies (0.1 ml-2.0 ml) (Teramato et al., 1999; Jobin et al., 2007).

| FLOW RATE | | | VOLUME (ML) AT SELECTED DURATIONS (SEC) | | | | |
|---|---|---|---|---|---|---|---|
| ML PER MIN | ML PER SEC | 0.5 SEC | 1 SEC | 1.5 SEC | 2.0 SEC | 2.5 SEC | 3.0 SEC |
| 1.00 | 0.02 | 0.01 | 0.02 | 0.03 | 0.04 | 0.05 | 0.06 |
| 2.00 | 0.03 | 0.02 | 0.03 | 0.05 | 0.07 | 0.08 | 0.10 |
| 4.00 | 0.07 | 0.03 | 0.07 | 0.10 | 0.13 | 0.17 | 0.20 |
| 8.00 | 0.13 | 0.07 | 0.13 | 0.20 | 0.27 | 0.33 | 0.40 |
| 16.00 | 0.27 | 0.13 | 0.27 | 0.40 | 0.53 | 0.67 | 0.80 |
| 32.00 | 0.53 | 0.27 | 0.53 | 0.80 | 1.07 | 1.33 | 1.60 |
| 64.00 | 1.07 | 0.53 | 1.07 | 1.60 | 2.13 | 2.67 | 3.20 |
| 128.00 | 2.13 | 1.07 | 2.13 | 3.20 | 4.27 | 5.33 | 6.40 |
| 256.00 | 4.27 | 2.13 | 4.27 | 6.40 | 8.53 | 10.67 | 12.80 |
| 512.00 | 8.53 | 4.27 | 8.53 | 12.80 | 17.07 | 21.33 | 25.60 |

Stimuli at low flow rates or volumes are not always sufficient to elicit a swallow to a single stimulus burst. Nonetheless, these sub-threshold stimuli deliver a bolus that remains in the pharynx until swallowed. To avoid any additive influence of preceding stimuli, the pharynx should be cleared by voluntary swallow or suction after each sub-threshold stimulus before a new stimulus can be delivered. This process is cumbersome and time consuming. As an alternative, an adaptive Bekesy-type threshold determination method is used, using a 1 up-1 down staircase to determine swallow threshold at each flow rate. The stimulus sequence begins at 0.5 sec, and stepped up between successive stimuli at 0.5 sec increments until a swallow or other threshold event occurred. At this "reversal point", stimulus duration is stepped down by 0.5 sec until no response is observed. This "staircase" process is repeated with the reversal points progressively bracketing the actual threshold. It is estimated that thresholds for 10 flow rates can be obtained using this method in less than 1 hour, resulting in a range of acceptable flow rates, stimulus durations, and volume thresholds.

After thresholds have been determined in the upright position, subjects assume a supine position and threshold stimuli are redelivered to the awake subject. Additional subject feedback is collected to determine which flow rates and volumes are most comfortable while supine and considered by the subject to be least likely to arouse them during sleep.

Example 3

Evaluation by Polysomnography

Polysomnographic recording methods, terminology, and scoring rules for sleep-related events are based on AASM guidelines (Iber et al., 2007). These are used to evaluate the effectiveness of a swallow stimulus for sleep apnea. All procedures are carried out by experienced sleep lab personnel. Acquired data includes EEG, EOG, submental EMG, ECG, thermistor-based nasal and oral airflow, nasal air pressure, pulse oximetry, respiratory inductance plethysmography at ribcage and abdomen, and body position.

The sleep EEG is derived by default from positions C3 and C4, using the contralateral mastoid (M1) as reference. Additional electrodes at F4 and O2, also relative to M1, are recommended by AASM guidelines. The electrooculogram (EOG) are derived from electrodes at E1 (lower left canthus) and E2 (upper right canthus) relative to M2. Submental EMG is recorded using one electrode placed at midline above the chin and 2 lateral electrodes placed below the chin. The subject is monitored at all times by experienced sleep laboratory personnel.

Sleep, respiratory, and swallow related variables are acquired across all subjects and treatments.
Sleep Architecture Per Session:
 1. Recording time
 2. Total sleep time (TST)
 3. Sleep efficiency
 4. Sleep threshold
 5. REM threshold
 6. Wake threshold
 7. Number of arousals
 8. Number of stage 0 (wake) periods
 9. % Stage 1 sleep
 10. % Stage 2 sleep
 11. % Stage 3 and/or 4 sleep (SWS)
 12. % REM sleep
 13. Number of REM periods Cardiorespiratory Variables Per Session:
1. AHI
2. Apnea Index
3. Hypopnea Index
4. Duration of apnea/hypopnea
5. Mean, minimum, and maximum oxygen saturation
6. Mean, minimum, and maximum respiration rate
7. Mean, minimum, and maximum heart rate
8. Mean saturation change in apnea/hypopnea
9. Number of desaturations ≥4%
10. Number of desaturations ≥10%
11. Length of desaturations ≥4%
12. Length of desaturations ≥10%
13. % apnea/hypopnea (duration/TST)
14. Arousal index (n per hour TST)
15. Swallow index (n per hour TST)
16. Expiratory reflex index (n per hour TST)

Event-by-Event (Stimulus-Related) Variables:
1. Swallow reflex, as indicated by submental EMG, airflow, video, and respiratory inductance plethysmography.
2. Expiratory reflex (e.g. expiration, cough, sneeze) as indicated by submental EMG, airflow, video, and respiratory inductance plethysmography.
3. Apnea, including respiratory effort, $SpO_2$, and airflow.
4. Arousals, as indicated by increased respiratory rate, increased heart rate, or lighter sleep stage as measured by polysomnography.

Event-by-event analysis is comparable to that used by Page and Jeffrey (1998). Each stimulus is classified according to the sleep stage in the 1 minute epoch immediately prior to delivery. The epoch immediately before the stimulus serves as a control and the epoch immediately after as a treatment period for each stimulus. The effect of stimulation is made by comparing events in these epochs. For example, respiratory rate, heart rate, SpO2 are averaged for the control period and treatment periods and quantified as % change.

Categorical events observed in the treatment period, such as swallow, arousal, or expiratory reflex are expressed as % of total number of stimuli. The effect of treatment group and sleep state on occurrence of categorical events in the treatment period is determined using $\chi 2$ test. The effect of treatment group and sleep state on categorical events in the control period is determined in the same manner.

It will be readily apparent to those skilled in the art that other suitable modifications and adaptations of the methods of the present disclosure described herein are obvious and may be made using suitable equivalents without departing from the scope of the present disclosure or the embodiments disclosed herein. The disclosures of all journal references, U.S. patents and publications referred to herein are hereby incorporated by reference in their entireties.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A method for treating and/or preventing a disorder in a subject in need thereof, the method comprising:
   delivering one or more stimulations to modulate one or more reflexes chosen from all or part of a swallowing reflex, all or part of a negative-pressure reflex, and combinations thereof, wherein:
   the disorder comprises one or more of: obstructive apnea, central apnea, mixed apnea, snoring, flow limitation, obesity hypoventilation syndrome, dysphagia, esophageal reflux, laryngeal reflux, pharyngeal reflux presence of unswallowed bolus, acid reflux, Gastro-Esophageal Reflux Disease (GERD), and combinations thereof;
   the one or more stimulations are delivered with subthreshold parameters insufficient to independently elicit the one or more reflexes in order to reduce a threshold of the one or more reflexes and enhance the subject's detection of sensory signals so as to trigger the one or more reflexes; and
   the one or more stimulations are delivered either according to a predetermined schedule, in response to one or more stimulation signals, and combinations thereof.

2. The method of claim 1, wherein the one or more stimulations comprise an electrical stimulation, a mechanical stimulation, or both.

3. The method of claim 2, wherein:
   the electrical stimulation is delivered to a reflex-related nerve, a reflex-related muscle, a reflex-related sensory receptor, and combinations thereof; and/or
   the mechanical stimulation is delivered to a reflex-related sensory receptor.

4. The method of claim 3, wherein:
   the reflex-related nerve comprises:
      an afferent chosen from: internal branch of the superior laryngeal nerve (iSLN), pharyngeal branch of vagus nerve, pharyngeal branch of glossopharyngeal nerve, tonsular branch of glossopharyngeal nerve, lingual branch of glossopharyngeal nerve, intermediate nerve, palantine nerve, greater petrosal nerve, any branch of facial nerve, and pterygopalatine nerve of trigeminal nerve; or
      an efferent chosen from: recurrent laryngeal nerve, external branch of superior laryngeal nerve, brancial motor branch of glossopharyngeal nerve and proximal fibers, mandibular nerve, medial pterygoid nerve, pharyngeal branch of vagus nerve and proximal fibers; branch of facial nerve and proximal fibers, and branch of hypoglossal nerve and proximal fibers; and
   the reflex-related sensory receptor is situated in skin or mucosa of the subject, and is chosen from:
      a mechanoreceptor sensitive to negative airway pressure, positive airway pressure, stretch, position, shear, slip, vibration, texture, touch, mechanical compression, muscle stretch, muscle drive, air flow, blood pressure or blood osmolarity;
      a chemoreceptor sensitive to $CO_2$, $O_2$, or pH;
      a thermoreceptor sensitive to temperature or airflow;
      a nociceptor sensitive to polymodal pain; and
      combinations thereof.

5. The method of claim 4, wherein the one or more stimulations are chosen from:
   a subthreshold electrical stimulation delivered to the reflex-related nerve or to the reflex-related sensory receptor to reduce the threshold of the reflex, to maintain muscle tone, and combinations thereof;
   a subthreshold electrical stimulation delivered to the reflex-related muscle to maintain muscle tone; and
   a subthreshold mechanical stimulation delivered to the reflex-related sensory receptor to reduce the threshold of the one or more reflexes.

6. The method of claim 5, wherein the one or more stimulations are delivered according to a delivery schedule chosen from periodic, random, or continuous.

7. The method of claim 6, wherein the one or more stimulation signals are received from a patient monitor device.

8. The method of claim 6, further comprising assessing one or more conditions of the subject chosen from a respiratory condition, a deglutition condition, a vibration condition, a reflux condition, and combinations thereof to predict the occurrence of the disorder in the subject, wherein:
the respiratory condition comprises apnea, tachypnea, hyperpnea, hypopnea, polypnea, dyspnea, bradypnea, cough, Cheyne-Stokes respiration, Biot's respiration, ataxic respiration, Kussmaul respiration, wheezing, irregular respiration, respiratory arrest, restrictive respiration, shallow breathing, hypoventilation and combinations thereof;
the deglutition condition comprises presence of unswallowed bolus, occurrence of swallow, occurrence of dysphagic swallow, presence of acid reflux, and combinations thereof;
the vibration condition comprises snoring, stridor, wheezing, vocalization, and combinations thereof; and
the reflux condition comprises esophageal reflux, pharyngeal reflux, laryngeal reflux, and combinations thereof.

9. The method of claim 8, further comprising:
obtaining one or more neural signals from one or more upper airway afferents of the subject;
processing each of the one or more neural signals to obtain two or more neural activity profiles, each neural activity profile characterized by one or more: a neural signal timing, a neural signal amplitude, a neural signal phase, a neural signal position, a neural signal conduction velocity, and combinations thereof;
comparing each of the neural activity profiles to one or more activity criteria to associate each neural activity profile with an associated activity type chosen from a respiratory activity type, a deglutition activity type, a vibration activity type, a reflux activity type, and combinations thereof, wherein at least one neural activity profile includes a first activity type and at least another neural activity profile includes a second activity type, the first activity type being different than the second activity type;
processing each of the neural activity profiles to determine an activity state characterizing the associated activity type, the activity state comprising:
 i. a respiratory state comprising respiratory timing, respiratory amplitude, respiratory phase, respiratory location, and combinations thereof;
 ii. a deglutition state comprising solid contact, fluid contact, contact velocity, contact timing, contact amplitude, contact pressure, contact texture, contact temperature, a presence of a unswallowed bolus, and combinations thereof;
 iii. a vibration state comprising vibration timing, vibration amplitude, vibration phase, vibration location, vibration pattern, and combinations thereof;
 iv. a reflux state comprising reflux timing, reflux pH, reflux location, and combinations thereof; and
 v. combinations thereof; and
processing the activity state of the subject to obtain the one or more conditions of the subject.

10. The method of claim 9, further comprising:
generating the one or more stimulation signals when:
the disorder is predicted to time the delivery of the one or more stimulations to coincide with an occurrence of the disorder;
the respiratory phase is an exhalation phase to time the delivery of the one or more stimulations to coincide with an exhalation of the subject; and
combinations thereof.

11. A system for treating and/or preventing a disorder in a subject in need thereof, the system comprising:
at least one processor; and
a disorder treatment application comprising a plurality of modules executable on the at least one processor, the plurality of modules comprising:
 a reflex stimulation module configured to provide instructions to the at least one processor in order to cause deliver of one or more stimulations to modulate one or more reflexes chosen from a swallowing reflex, a negative-pressure reflex, and combinations thereof, wherein:
  the disorder is chosen from obstructive apnea, central apnea, mixed apnea, snoring, flow limitation, obesity hypoventilation syndrome, dysphagia, esophageal reflux, laryngeal reflux, pharyngeal reflux, presence of unswallowed bolus, acid reflux, Gastro-Esophageal Reflux Disease (GERD), and combinations thereof;
  the one or more stimulations are delivered with parameters chosen from subthreshold parameters insufficient to independently elicit the one or more reflexes in order to reduce a threshold of the one or more reflexes and enhance the subject's detection of sensory signals so as to trigger the one or more reflexes; and
  the one or more stimulations are delivered in response to one or more stimulation signals.

12. The system of claim 11, wherein:
the one or more stimulations comprise an electrical stimulation, a mechanical stimulation, or both;
the electrical stimulation is a delivered to a reflex-related nerve, a reflex-related muscle, and combinations thereof; and/or
the mechanical stimulation is delivered to a reflex-related sensory receptor.

13. The system of claim 12, wherein the one or more stimulations are chosen from:
a subthreshold electrical stimulation delivered to the reflex-related nerve or to the reflex-related sensory receptor to reduce the threshold of the reflex, to maintain muscle tone, and combination thereof;
a subthreshold electrical stimulation delivered to the reflex-related muscle to maintain muscle tone; and
a subthreshold mechanical stimulation delivered to the reflex-related sensory receptor to reduce the threshold of the one or more reflexes.

14. The system of claim 11, wherein the plurality of modules further comprises a stimulation timing module configured to provide instructions to the at least one processor in order to time the delivery of each of the one or more stimulations according to a predetermined schedule, in response to at least one stimulation signal, and combinations thereof.

15. The system of claim 14, wherein the one or more stimulation signals are received from a patient monitor system.

16. The system of claim 14, wherein the plurality of modules further comprises a disorder prediction module configured to provide instructions to the at least one processor in order to assess one or more conditions of the subject chosen from a respiratory condition, a deglutition condition, a vibration condition, a reflux condition, and combinations thereof to predict the occurrence of the disorder in the subject, wherein:
- the respiratory condition comprises apnea, tachypnea, hyperpnea, hypopnea, polypnea, dyspnea, bradypnea, cough, Cheyne-Stokes respiration, Biot's respiration, ataxic respiration, Kussmaul respiration, wheezing, irregular respiration, respiratory arrest, restrictive respiration, shallow breathing, hypoventilation and combinations thereof;
- the deglutition condition comprises presence of unswallowed bolus, occurrence of swallow, occurrence of dysphagic swallow, presence of acid reflux, and combinations thereof;
- the vibration condition comprises snoring, stridor, wheezing vocalization, and combinations thereof; and
- the reflux condition comprises esophageal reflux, pharyngeal reflux, laryngeal reflux, and combinations thereof.

17. The system of claim 16, wherein the plurality of modules further comprises:
- a neural signal acquisition module configured to provide instructions to the at least one processor in order to obtain one or more neural signals from one or more upper airway afferents of the subject;
- a neural activity profile module configured to provide instructions to the at least one processor in order to process each of the one or more neural signals to obtain two or more neural activity profiles, each neural activity profile characterized by one or more: a neural signal timing, a neural signal amplitude, a neural signal phase, a neural signal position, a neural signal conduction velocity, and combinations thereof; and
- an activity type module configured to provide instructions to the at least one processor in order to compare each of the neural activity profiles to one or more activity criteria to associate each neural activity profile with an associated activity type chosen from a respiratory activity type, a deglutition activity type, a vibration activity type, a reflux activity type, and combinations thereof, wherein at least one neural activity profile includes a first activity type and at least another neural activity profile includes a second activity type, the first activity type being different than the second activity type.

18. The system of claim 17, wherein the plurality of modules further comprises an activity state module configured to provide instructions to the at least one processor in order to process each of the at least one neural activity profiles to determine an activity state characterizing the associated activity type, the activity state comprising a respiratory state comprising respiratory timing, respiratory amplitude, respiratory phase, respiratory location, and any combination thereof, and wherein the stimulation timing module provides the instructions to the at least one processor in order to generate the one or more stimulation signals when:
- the disorder prediction module predicts the disorder, to time the delivery of the one or more stimulations to coincide with an occurrence of the disorder;
- the activity state module is configured to determine that the respiratory phase is an exhalation phase, to time the delivery of the one or more stimulations to coincide with an exhalation of the subject; and
- combinations thereof.

19. The system of claim 11, further comprising:
- a graphical user interface (GUI) module configured to provide instructions to the at least one processor in order to generate one or more forms used to receive inputs to the system and configured to deliver outputs from the system.

* * * * *

UNITED STATES PATENT AND TRADEMARK OFFICE
CERTIFICATE OF CORRECTION

PATENT NO. : 10,463,266 B2
APPLICATION NO. : 15/623712
DATED : November 5, 2019
INVENTOR(S) : Willard Wilson Page 1 of 1

It is certified that error appears in the above-identified patent and that said Letters Patent is hereby corrected as shown below:

In the Claims

In Column 46, Line 17:
Replace "deliver"
With --delivery--

In Column 48, Line 34:
Delete "configured"

Signed and Sealed this
Eleventh Day of February, 2020

Andrei Iancu
*Director of the United States Patent and Trademark Office*